(12) United States Patent
Alhadeff et al.

(10) Patent No.: US 11,596,608 B2
(45) Date of Patent: Mar. 7, 2023

(54) FORMULATION

(71) Applicant: INDEX PHARMACEUTICALS AB, Solna (SE)

(72) Inventors: Paul Alhadeff, Solna (SE); Christine Dieterich Johansson, Täby (SE); Peter Zerhouni, Stockholm (SE); Wei Tian, Cleghorn (GB); Graeme William Andrew Hamilton Johnston, Blantyre (GB)

(73) Assignee: Index Pharmaceuticals AB, Solna (SE)

( * ) Notice: Subject to any disclaimer, the term of this patent is extended or adjusted under 35 U.S.C. 154(b) by 17 days.

(21) Appl. No.: 17/052,435

(22) PCT Filed: May 3, 2019

(86) PCT No.: PCT/EP2019/061443
§ 371 (c)(1),
(2) Date: Nov. 2, 2020

(87) PCT Pub. No.: WO2019/211466
PCT Pub. Date: Nov. 7, 2019

(65) Prior Publication Data
US 2021/0338592 A1     Nov. 4, 2021

(30) Foreign Application Priority Data
May 3, 2018   (GB) ..................... 1807312

(51) Int. Cl.
| C07H 21/04 | (2006.01) |
| A61K 9/48 | (2006.01) |
| A61K 9/00 | (2006.01) |
| A61K 31/7125 | (2006.01) |

(52) U.S. Cl.
CPC .......... *A61K 9/4825* (2013.01); *A61K 9/0053* (2013.01); *A61K 9/4858* (2013.01); *A61K 9/4866* (2013.01); *A61K 9/4891* (2013.01); *A61K 31/7125* (2013.01)

(58) Field of Classification Search
None
See application file for complete search history.

(56) References Cited

U.S. PATENT DOCUMENTS

| 5,366,878 A | 11/1994 | Pederson et al. |
| 5,635,377 A | 6/1997 | Pederson et al. |
| 8,895,522 B2 | 11/2014 | Von Stein et al. |

FOREIGN PATENT DOCUMENTS

| EP | 2595806 | 11/2019 |
| WO | WO2007/050034 | 5/2007 |
| WO | WO2008/063910 | 5/2008 |
| WO | WO2010/003430 | 1/2010 |
| WO | WO2013/076262 | 5/2013 |
| WO | WO2018/206711 | 11/2018 |
| WO | WO2018/206713 | 11/2018 |
| WO | WO2018/206722 | 11/2018 |

OTHER PUBLICATIONS

Capryol HPMG CAS ID 31565-12-5, 1984, in 1 page.
D'Haens et al., "A Review of Activity Indices and Efficacy End Points for Clinical Trials of Medical Therapy in Adults With Ulcerative Colitis," Gastroenterology 2007, 132, 763-786.
Domènech et al., "An Overview of the Natural History of Inflammatory Bowel Diseases," Digestive Diseases 2014, 32(4), 320-327.
Fausel & Afzali, "Biologics in the management of ulcerative colitis—comparative safety and efficacy of TNF-α antagonists," Therapeutics and Clinical Risk Management 2015, 11, 63-73.
Feagan et al., "Vedolizumab as Induction and Maintenance Therapy for Ulcerative Colitis," The New England Journal of Medicine 2013, 369(8), 699-710.
Geboes et al., "A reproducible grading scale for histological assessment of inflammation in ulcerative colitis," Gut 2000, 47, 404-409.
International Search Report and Written Opinion dated Jul. 18, 2019 in PCT Application No. PCT/EP2019/061443.
Irvine, "Quality of Life of Patients with Ulcerative Colitis: Past, Present, and Future," Inflammatory Bowel Disease 2008, 14(4), 554-565.
Khan et al., "Efficacy of Immunosuppressive Therapy for Inflammatory Bowel Disease: A Systematic Review and Meta-Analysis," The American Journal of Gastroenterology 2011, 106(4), 630-642.
Love, "Pharmacotherapy for Moderate to Severe Inflammatory Bowel Disease: Evolving Strategies," The American Journal of Managed Care 2016, 22(3), S39-S50.
Musch et al., "Topical Treatment with the Toll-like Receptor Agonist DIMS0150 Has Potential for Lasting Relief of Symptoms in Patients with Chronic Active Ulcerative Colitis by Restoring Glucocorticoid Sensitivity," Inflammatory Bowel Disease 2013, 19(2), 283-292.
Peyrin-Biroulet et al., "Defining Disease Severity in Inflammatory Bowel Diseases: Current and Future Directions," Clinical Gastroenterology and Hepatology 2016, 14, 348-354.
Prantera, "Glucocorticosteroids in the treatment of inflammatory bowel disease and approaches to minimizing systemic activity," Therapeutic Advances in Gastroenterology 2013, 6(2), 137-156.
Rachmilewitz, "Coated mesalazine (5-aminosalicylic acid) versus sulphasalazine in the treatment of active ulcerative colitis: a randomised trial," BMJ 1989, 298, 82-86.
Schroeder et al., "Coated Oral 5-Aminosalicylic Acid Therapy for Mildly to Moderately Active Ulcerative Colitis," The New England Journal of Medicine 1987, 317(26), 1625-1629.
Stange et al., "European evidence-based Consensus on the diagnosis and management of ulcerative colitis: Definitions and diagnosis," Journal of Chron's and Colitis 2008, 2, 1-23.

(Continued)

*Primary Examiner* — Kimberly Chong
(74) *Attorney, Agent, or Firm* — Sheppard, Mullin, Richter & Hampton LLP

(57) ABSTRACT

The present invention relates a formulation and capsule suitable for oral administration. The invention further relates to the use of the formulation and capsule for treating inflammatory bowel diseases, for instance ulcerative colitis (UC) or Crohn's disease.

24 Claims, 7 Drawing Sheets
Specification includes a Sequence Listing.

(56) References Cited

OTHER PUBLICATIONS

Sutherland et al., "5-Aminosalicylic Acid Enema in the Treatment of Distal Ulcerative Colitis, Proctosigmoiditis, and Proctitis," Gastroenterology 1987, 92, 1894-1898.

Travis et al., "Review article: defining remission in ulcerative colitis," Alimentary Pharmacology and Therapeutics 2011, 34, 113-124.

Travis et al., "European evidence-based Consensus on the management of ulcerative colitis: Current management," Journal of Crohn's and Colitis 2008, 2, 24-62.

Ungar & Kopylov, "Advances in the development of new biologies in inflammatory bowel disease," Annals of Gastroenterology 2016, 29, 243-248.

U.S. National Library of Medicine, "The Efficacy of Cobitolimod in Patients With Moderate to Severe Active Ulcerative Colitis," 2018, in 8 pages. https://clinicaltrials.gov/ct2/show/NCT0317866.

Atreya et al., "Clinical Effects of a Topically Applied Toll-like Receptor 9 Agonist in Active Moderate-to-Severe Ulcerative Colitis," Journal of Crohn's and Colitis 2016, 1294-1302.

FORMULATION

RELATED APPLICATIONS

The present application is a U.S. national phase application under 35 U.S.C. § 371 of International Application No. PCT/EP2019/061443, filed on May 3, 2019 and published as WO 2019/211466 A1 on Nov. 7, 2019, which claims priority to GB Application No. 1807312.2, filed on May 3, 2018. The content of each of these related applications is incorporated herein by reference in its entirety.

REFERENCE TO SEQUENCE LISTING

The present application includes a Sequence Listing in electronic format. The Sequence Listing is provided as a file entitled Sequence Listing 63CZ-312121-US, created Feb. 15, 2021, which is 1 kilobyte in size. The information in the electronic format of the Sequence Listing is incorporated herein by reference in its entirety.

FIELD OF THE INVENTION

The present invention relates a formulation and capsule suitable for oral administration. The invention further relates to the use of the formulation and capsule for treating inflammatory bowel diseases.

BACKGROUND OF THE INVENTION

A number of inflammatory conditions may affect the intestines (small intestine, colon and rectum). Inflammatory bowel disease is an example of such a condition. These conditions may be treated with oligonucleotides, in particular oligonucleotides containing a CpG dinucleotide. These oligonucleotides bind to receptors on cells such as immune cells and/or epithelial cells thereby mediating the immune response, and alleviating inflammation.

Inflammatory bowel disease (IBD) refers to a group of inflammatory conditions of the colon and the small intestine. The major types of IBD are ulcerative colitis (UC) and Crohn's disease. The main difference between UC and Crohn's disease is the location and nature of the inflammatory changes. Crohn's disease can affect any part of the gastrointestinal tract, from mouth to anus, while UC is most often restricted to the colon and the rectum.

Ulcerative colitis (UC) is a disease characterized by chronic inflammation of the rectal and colonic mucosa, affecting the innermost lining in the first stage. The disease is recurrent, with both active and inactive stages that differ in pathology, symptoms and treatment. The underlying cause of UC is not understood, nor is it known what triggers the disease to recur between its inactive and active forms (Irvine, E. J. (2008) Inflamm Bowel Dis 14(4): 554-565). Symptoms of active UC include progressive loose stools with blood and increased frequency of bowel movements. Active mucosal inflammation is diagnosed by endoscopy.

The stools contain pus, mucous and blood and are often associated with abdominal cramping with urgency to evacuate (tenesmi). Diarrhoea may have an insidious onset or, more rarely, start quite suddenly. In severe cases the symptoms may include fever and general malaise. In severe stages, deep inflammation of the bowel wall may develop with abdominal tenderness, tachycardia, fever and risk of bowel perforation. Furthermore, patients with UC may suffer extra intestinal manifestations such as arthralgia and arthritis, erythema nodosum, pyoderma gangrenosum and inflammation in the eyes. In the case of remission or inactive UC, patients are usually free of bowel symptoms.

The extent of inflamed and damaged mucosa differs among patients with UC. UC that affects only the rectum is termed ulcerative proctitis. The condition is referred to as distal or left sided colitis when inflammatory changes are present in the left side of the colon up to the splenic flexure. In extensive UC the transverse colon is also affected, and pancolitis designates a disease involving the entire colon.

Active mucosal inflammation is diagnosed by endoscopy and is characterized by a loss of vascular patterning, oedema, petechia, spontaneous bleeding and fibrinous exudates. The endoscopic picture is that of continuous inflammation, starting in the rectum and extending proximally to a variable extent into the colon. Biopsies obtained at endoscopy and subjected to histological examination help to diagnose the condition. Infectious causes, including *Clostridium difficile*, camphylobacter, *Salmonella* and *Shigella*, may mimic UC and can be excluded by stool cultures.

The treatment of patients with active UC aims to reduce inflammation and promote colon healing and mucosal recovery. In milder cases the disease may be controlled with conventional drugs including sulphasalazine, 5-aminosalicylic acid (5-ASA) (Sutherland, L., F. Martin, S. Greer, M. Robinson, N. Greenberger, F. Saibil, T. Martin, J. Span, E. Prokipchuk and L. Borgn (1987) Gastroenterology 92: 1894-1898) and glucocorticosteroids (GCS) (Domenech, E., M. Manosa and E. Cabre (2014). Dig Dis 32(4): 320-327).

GCS are generally used to treat disease flare-ups, but there are significant side effects in long-term use, and the possible development of steroid dependent disease. Glucocorticoid drugs act non-selectively, so in the long run they may impair many healthy anabolic processes (Prantera, C. and S. Marconi (2013) Therap Adv Gastroenterol 6(2): 137-156).

For patients who become refractory to GCS and suffer from severe or moderately severe attacks of UC, the addition of immunomodulatory agents such as cyclosporine, 6-mercaptopurine and azathioprine may be used. However, immunomodulators are slow-acting and the induction of remission in these patients is often temporary (Khan, K. J., M. C. Dubinsky, A. C. Ford, T. A. Ullman, N. J. Talley and P. Moayyedi (2011) Am J Gastroenterol 106(4): 630-642).

Further treatment options for UC include biologic agents (Fausel, R. and A. Afzali (2015) Ther Clin Risk Manag 11: 63-73). The three TNF-α inhibitors currently approved for the treatment of moderate to severe UC are infliximab, adalimumab, and golimumab. All three carry potential risks associated with their use, and should be avoided in certain patients, e.g. those with uncontrolled infections, advanced heart failure, neurologic conditions and in patients with a history of malignancy, due to a potential risk of accelerating the growth of a tumour. Other potential adverse effects of TNF-α inhibitor therapy include neutropenia, hepatotoxicity, serum sickness, leukocytoclastic vasculitis, rash including psoriasiform rash, induction of autoimmunity, and injection or infusion site reactions, including anaphylaxis, convulsions, and hypotension.

All three TNF-α inhibitor agents and their related biosimilar/derivative counterparts may be used to induce and maintain clinical response and remission in patients with UC. Combination therapy with azathioprine is also used for inducing remission. However, more than 50% of patients receiving TNF-α inhibitor agents fail to respond to induction dosing, or lose response to the TNF-α inhibitor agents over time (Fausel, R. and A. Afzali (2015) Ther Clin Risk Manag 11: 63-73).

Vedolizumab, a α4β7 integrin inhibitor, was recently approved for the treatment of UC. In the GEMINI 1 trial, vedolizumab was found to be more effective than placebo for inducing and maintaining clinical response, clinical remission, and mucosal healing (Feagan, B. G., P. Rutgeerts, B. E. Sands, S. Hanauer, J. F. Colombel, W. J. Sandborn, G. Van Assche, J. Axler, H. J. Kim, S. Danese, I. Fox, C. Milch, S. Sankoh, T. Wyant, J. Xu, A. Parikh and G. S. Group (2013). "Vedolizumab as induction and maintenance therapy for ulcerative colitis." *N Engl J Med* 369(8): 699-710.). Further treatment options for ulcerative colitis include JAK inhibitors, such as tofacitinib.

Ulcerative colitis patients, who are chronically active and refractory to known treatments pose a serious medical challenge and often the only remaining course of action is colectomy. A total colectomy is a potentially curative option in severe UC, but is a life-changing operation that entails risks as complications, such as pouch failure, pouchitis, pelvic sepsis, infertility in women, and nocturnal faecal soiling, may follow. Therefore, surgery is usually reserved for patients with severe refractory disease, surgical or other emergencies, or patients with colorectal dysplasia or cancer.

An emergent third line treatment for UC is cobitolimod (Kappaproct/DIMS0150), a modified single strand deoxyribonucleic acid (DNA)-based synthetic oligonucleotide of 19 bases in length. Cobitolimod has the sequence 5'-G*G*A*ACAGTTCGTCCAT*G*G*C-3' (SEQ ID NO:1), wherein the CG dinucleotide is unmethylated. An asterisk (*) represents a phosphorothioate modification.

Cobitolimod functions as an immunomodulatory agent by targeting the Toll-like receptor 9 (TLR9) present in immune cells or on the surface of intestinal epithelial cells. These immune cells i.e., B-cells and plasmacytoid dendritic cell (pDCs) reside in high abundance in mucosal surfaces, such as colonic and nasal mucosa. The immune system is the key mediator of the changes of UC. The mucosa of the colon and rectum of patients with UC is chronically inflamed and contains active immune cells.

Cobitolimod may be topically administered in the region of inflammation, which places the drug in close contact with a high number of intended target cells, ensuring that the drug will reach an area rich in TLR9 expressing cells. The activation of these cells by cobitolimod induces various cytokines, such as type I interferons and interleukin 10 (IL-10) which are classical anti-inflammatory cytokines and are believed to be important factors for the clinical effect of cobitolimod.

A range of non-clinical safety studies have been conducted with cobitolimod, as well as four clinical trials. The majority of the trials have involved administration of a relatively low (30 mg) dose of cobitolimod. Overall, data on cobitolimod support a positive benefit-risk assessment for patients with chronic active UC. Cobitolimod is safe and well tolerated and has been shown to be effective to induce clinical response and remission in patients with chronic active UC, as well as symptomatic and endoscopic remission in patients with treatment refractory, moderate to severe chronic active UC.

Present treatments using cobitolimod involve topical administration, for instance intracolonically as a rectal enema. Alternatively, cobitolimod may be administered during colonoscopy with the aid of a spraying catheter, or other suitable medical equipment, inserted though the colonoscopies biopsy channel. Rectal administration of cobitolimod directly to the site of the inflammation can require medical professionals, and therefore may present problems for patient compliance. Consequently a need exists for a formulation of cobitolimod suitable for oral administration, which is generally easier for patients to self-administer.

During the course of treatment, it is important for oral administration that the CpG-containing oligonucleotide, for example cobitolimod, is not released prematurely, e.g. in the mouth or stomach where it will have little effect on the area affected by inflammatory bowel disease. In other words, such a formulation must maximise topical exposure to the CpG-containing oligonucleotide at the relevant point in the gastrointestinal tract, for example in the ileum or in the colon. Therefore a suitable formulation should prevent release of the CpG containing oligonucleotide until the desired point in the digestive system.

SUMMARY OF THE INVENTION

It has now surprisingly been found that a formulation suitable for oral administration may be provided, the formulation comprising (i) an oligonucleotide containing a CpG dinucleotide and having 6 to 40 nucleotides, and (ii) esters which are monoesters and/or diesters of propylene glycol with caprylic acid or monoesters and/or diesters of glycerol with caprylic acid.

Preferably, the oligonucleotide comprises the sequence (SEQ ID NO: 2)
5'-GGAACAGTTCGTCCATGGC-3'.

This is based on the unexpected finding that esters which are monoesters and/or diesters of propylene glycol with caprylic acid or monoesters and/or diesters of glycerol with caprylic acid, for example propylene glycol caprylate esters, show high chemical compatibility with the oligonucleotides above as well as giving a formulation good dispersibility and minimal degradation over time. A large number of different carriers were tested and propylene glycol caprylate esters were found to provide the least degradation over time whilst also showing no alteration in dispersion characteristics. Further, this carrier is also able to release the oligonucleotide relatively quickly once the formulation is present in the desired area of the body.

The invention further provides a capsule suitable for oral administration, said capsule comprising:

a) a gelatin container, and within the container
b) a formulation as defined above.

The capsule according may further comprise c) a coating on the exterior surface of the container.

The presence of a coating allows the point at which the oligonucleotide is released within the body to be determined, for example based on the pH at a particular environment within the digestive system. In this way, the capsule does not release the oligonucleotide at a point where it will be ineffective for treating inflammatory bowel disease. The oligonucleotide is thereby targeted to the site of inflammation, usually the colon, to provide the most effective treatment.

The invention provides the formulation or capsule above for use in the treatment of an inflammatory bowel disease, in particular ulcerative colitis or Crohn's disease.

The invention also provides a method of treating inflammatory bowel disease in a subject, the method comprising orally administering to said subject a formulation or capsule as defined herein.

The invention also provides the use of a formulation or a capsule as defined herein for the manufacture of a medicament for treatment of inflammatory bowel disease.

DETAILED DESCRIPTION OF THE INVENTION

Figure 1:
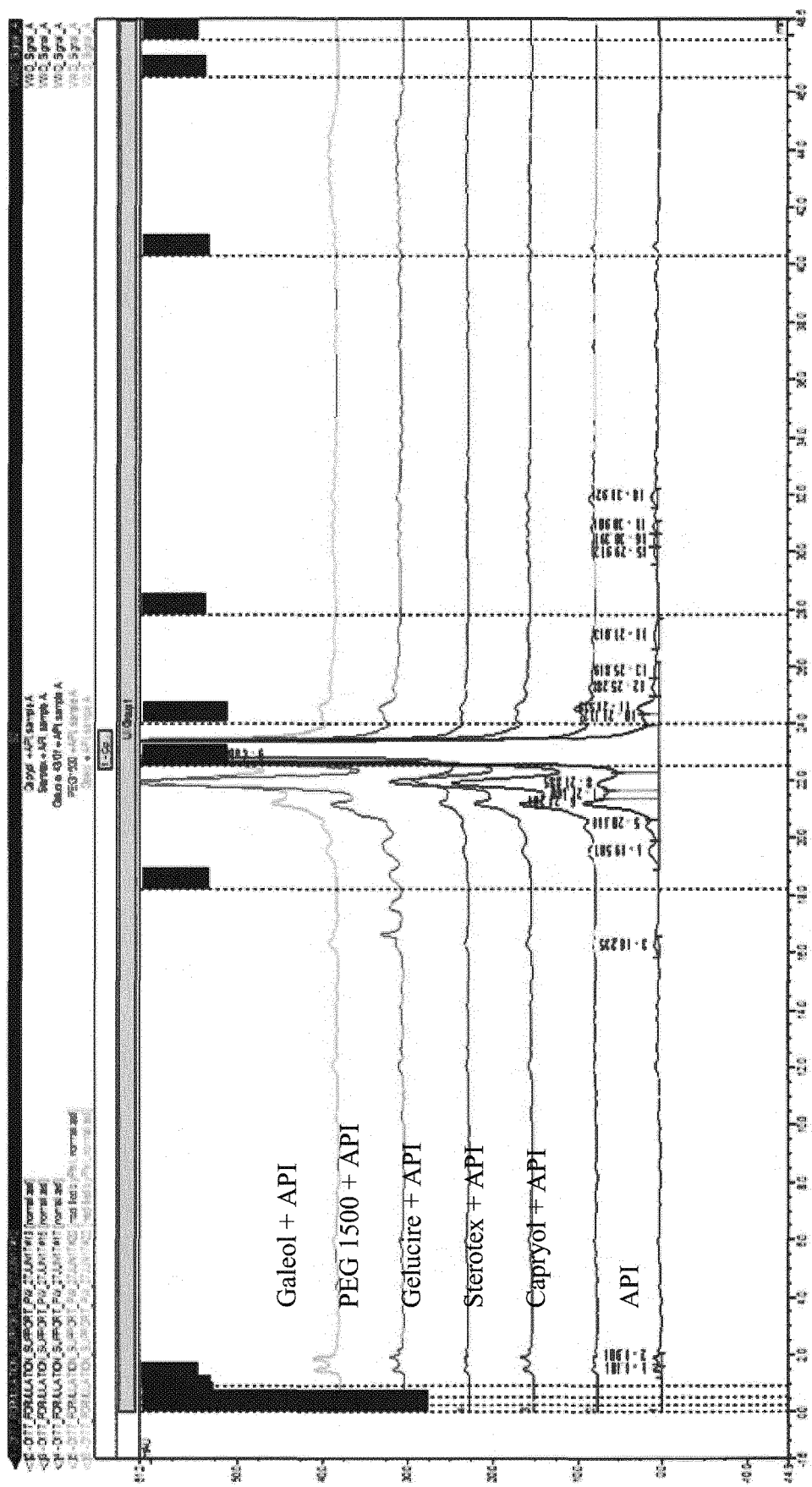
FIG. 1 shows a chromatogram comparing the cobitolimod standard to the 5 binary mixes prepared with different excipients (Capryol, Sterotex, Gelucire, PEG 1500 and Geleol) at the initial time point.

All patents, patent applications, and publications cited herein are hereby incorporated by reference in their entirety.

The present invention provides a formulation suitable for oral administration comprising an oligonucleotide containing a CpG dinucleotide and having 6 to 40 nucleotides, preferably an oligonucleotide comprising the sequence 5'-GGAACAGTTCGTCCATGGC-3' (SEQ ID NO:2), and propylene glycol caprylate esters.

As used herein, the term "oligonucleotide" refers to a polynucleoside formed from a plurality of linked individual nucleoside units. Such oligonucleotides can be obtained from existing nucleic acid sources, including genomic DNA or cDNA, plasmids, vectors, or bacterial DNA, but are preferably produced by synthetic methods. The nucleoside residues can be coupled to each other by any of the numerous known internucleoside linkages. Such internucleoside linkages include, without limitation, the natural internucleoside phosphodiester bond or indeed modified internucleosides such as, but not limited to, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkages (e. g., (Rp)- or (Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers. The alkyl linker may be branched or unbranched, substituted or unsubstituted, and chirally pure or a racemic mixture.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. The modified nucleoside may be a non-natural pyrimidine or purine nucleoside, as herein described. The modified nucleoside may be a 2'-substituted ribonucleoside, an arabinonucleoside or a 2'-deoxy-2'-substituted-arabinoside.

As used herein, the term "a hybrid oligonucleotide" is an oligonucleotide having more than one type of nucleoside.

Herein, the term "oligonucleotide" includes hybrid and chimeric oligonucleotides. A "chimeric oligonucleotide" is an oligonucleotide having more than one type of internucleoside linkage within its sequence structure. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (U.S. Pat. Nos. 5,635,377 and 5,366,878).

Herein, the term "oligonucleotide" also includes circularized variants and circular oligonucleotides.

Preferably, the oligonucleotide comprises at least one naturally occurring phosphodiester, or one modified phosphorothioate, or phosphorodithioate internucleoside linkage, however preferred linkages or indeed backbone modifications including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, 2' OMe (OxyMethyl group at 2'position), carbonate, carbamate, morpholino, boranophosphonate, phosphoramidates, especially primary amino-phosphoramidates, N3 phosphoramidates and N5 phosphoramidates, and stereospecific linkages (e. g., (Rp)- or (Sp)-phosphorothioate, alkylphosphonate, or phosphotriester linkages) are also envisaged.

The sugar moiety of the nucleoside can be a non-naturally occurring sugar moiety. Herein, a "naturally occurring sugar moiety" is a sugar moiety that occurs naturally as part of a nucleic acid, e. g., ribose and 2'-deoxyribose, and a "non-naturally occurring sugar moiety" is any sugar that does not occur naturally as part of a nucleic acid, but which can be used in the backbone for an oligonucleotide, for example but not limited to hexose. Arabinose and arabinose derivatives are examples of preferred sugar moieties.

Modified or substituted oligonucleotides are often preferred over native forms because of desirable properties such as, for example, enhanced cellular uptake, enhanced affinity for nucleic acid target and increased stability in the presence of nucleases. An oligonucleotide is usually comprised of more than ten (10) and up to one hundred (100) or more deoxyribonucleotides or ribonucelotides, although preferably between about six (6) and forty (40), most preferably between about eight (8) and about twenty (20). The exact size will depend on many factors, which in turn depends on the ultimate function or use of the oligonucleotide. The oligonucleotide may be generated in any manner, including chemical synthesis, DNA replication, reverse transcription, or a combination thereof.

A CpG dinucleotide is a cytosine triphosphate deoxynucleotide (i.e. "C") joined to a guanine triphosphate deoxynucleotide (i.e. "G") by a phosphodiester bond (i.e. "p"). The C and G moieties with the CpG dinucleotide are orientated such that the C moiety is closer to the 5'-end of the oligonucleotide and the G moiety is closer to 3'-end of the oligonucleotide. A CpG dinucleotide is also known as a "CpG motif" or a "CG dinucleotide". The CpG dinucleotide may be methylated or unmethylated, but is preferably unmethylated.

In one aspect of the present invention the oligonucleotide is an oligonucleotide having the sequence 5'-Xm-CG-Yn-3', wherein X is A, T, C or G, Y is A, T, C, or G, m is 0-38, n is 0-38, provided that the total length of the oligonucleotide is between 6 and 40 nucleotides.

Typically, in the oligonucleotide having the sequence above (5'-Xm-CG-Yn-3') m is 0-35 and n is 0-35, m is 0-30 and n is 0-30, m is 0-25 and n is 0-25, m is 0-20 and n is 0-20, m is 0-15 and n is 0-15, m is 0-12 and n is 0-12, m is 0-10 and n is 0-10, m is 0-8 and n is 0-8, m is 0-6 and n is 0-6, or m is 0-4 and n is 0-4, provided that the total length of the oligonucleotide is between 6 and 40 nucleotides.

Preferably, the oligonucleotide having the sequence above (5'-Xm-CG-Yn-3') m is 1-35 and n is 1-35, m is 1-30 and n is 1-30, m is 1-25 and n is 1-25, m is 1-20 and n is 1-20, m is 1-15 and n is 1-15, m is 1-12 and n is 1-12, m is 1-10 and n is 1-10, m is 1-8 and n is 1-8, m is 1-6 and n is 1-6, or m is 1-4 and n is 1-4, provided that the total length of the oligonucleotide is between 6 and 40 nucleotides.

More preferably, the oligonucleotide having the sequence above (5'-Xm-CG-Yn-3') m is 2-35 and n is 2-35, m is 2-30 and n is 2-30, m is 2-25 and n is 2-25, m is 2-20 and n is 2-20, m is 2-15 and n is 2-15, m is 2-12 and n is 2-12, m is 2-10 and n is 2-10, m is 2-8 and n is 2-8, m is 2-6 and n is 2-6, m is 2-4 and n is 2-4 or m is 2 and n is 2, provided that the total length of the oligonucleotide is between 6 and 40 nucleotides.

Typically, at least one CG dinucleotide in the oligonucleotide is unmethylated.

The oligonucleotide may therefore have the sequence 5'-GGAACAGTTCGTCCATGGC-3' (SEQ ID NO:2), wherein the CG dinucleotide is unmethylated. Alternatively, the oligonucleotide may have the sequence 5'-GGAACAGTTCGTCCATGGC-3' (SEQ ID NO:2), wherein the CG dinucleotide is methylated, preferably wherein the CG dinucleotide is methylated on the ribose unit of one or both nucleotides.

Typically, at least one nucleotide in said oligonucleotide has a backbone modification. Said backbone modification may be located in the 5'- and/or the 3'-end of said oligonucleotide.

Typically, the phosphate backbone modification may occur on the 5' inter-nucleotide linkages, or on the 3' inter-nucleotide linkages. The modification may occur at one or more nucleotides at any position along the entire length of said oligonucleotide.

Typically, at least one nucleotide in said oligonucleotide has a phosphate backbone modification. The backbone modification is typically a phosphorothioate or a phosphorodithioate modification.

The oligonucleotide may comprise at least one modified sugar moiety nucleobase. The modified sugar moiety may be a 2'-O-methoxyethyl sugar moiety.

Phosphorothioate linkages can be illustrated with asterisks (*) in a sequence, e.g. in the sequence: 5'-G*G*A*ACAGTTCGTCCAT*G*G*C-3' (SEQ ID NO:1), wherein the CG dinucleotide is unmethylated.

Preferably, said oligonucleotide has the sequence 5'-G*G*A*ACAGTTCGTCCAT*G*G*C-3' (SEQ ID NO:1), wherein the CG dinucleotide is unmethylated. Thus, preferably said oligonucleotide is cobitolimod. The formulation may comprise, consist essentially of or consist of an oligonucleotide containing a CpG dinucleotide and having 6 to 40 nucleotides, preferably an oligonucleotide comprising SEQ ID NO:2, more preferably cobitolimod, and esters which are monoesters and/or diesters of propylene glycol with caprylic acid or monoesters and/or diesters of glycerol with caprylic acidpropylene glycol caprylate esters.

The oligonucleotide containing a CpG dinucleotide and having 6 to 40 nucleotides, preferably an oligonucleotide comprising SEQ ID NO:2, more preferably cobitolimod, may be present in an amount of between 1 and 50% by weight of the formulation, or between 2 and 40% by weight, or between 3 and 30%, or between 4 and 25%, between 5 and 20%, between 10 and 15% or between 11 and 14% cobitolimod by weight. The oligonucleotide containing a CpG dinucleotide and having 6 to 40 nucleotides, preferably an oligonucleotide comprising SEQ ID NO:2, more preferably cobitolimod, may be present in the formulation in an amount of about 5% by weight, about 6% by weight, about 7% by weight, about 8% by weight, about 9% by weight, about 10% by weight, about 11% by weight, 11.5% by weight, about 12% by weight, about 13% by weight, about 14% by weight or about 15% by weight.

The esters used in the compositions of the present invention are monoesters and/or diesters of propylene glycol (also known as propane-1,2-diol) with caprylic acid, or monoesters and/or diesters of glycerol (also known as propane-1,2,3-triol) with caprylic acid. Capyrlic acid is also known as octanoic acid. Thus, the esters are (i) propylene glycol monocaprylate and/or propylene glycol dicaprylate, or (ii) glycerol monocaprylate and/or glycerol dicaprylate.

In the monoester of propylene glycol with caprylic acid, the ester link may be at the 1 position on propylene glycol (2-hyroxypropyl octanoate). In the monoester of propylene glycol with caprylic acid, the ester link may be at the 2 position on propylene glycol (1-hydroxypropan-2-yl octanoate).

Typically, the esters used in the invention are monoester and/or diesters of propylene glycol (i.e. propylene glycol monocaprylate [the monoesters of propylene glycol and caprylic acid] and/or propylene glycol dicaprylate [the diester of propylene glycol and caprylic acid]). Thus, it is preferred that the esters are propylene glycol caprylate esters.

The esters may comprise, consist essentially or consist of propylene glycol monocaprylate. Alternatively, the esters may comprise, consist essentially or consist of propylene glycol dicaprylate.

However, it is particularly preferred that the esters comprise a combination of both propylene glycol monocaprylate and propylene glycol dicaprylate. Typically, the esters comprise 10 to 90% by weight propylene glycol monocaprylate and 10 to 90% by weight propylene glycol dicaprylate relative to the total weight of esters. Preferably, the esters comprise between 55 and 80% by weight propylene glycol monocaprylate and between 20 and 45% by weight propylene glycol dicaprylate, relative to the total weight of esters. More preferably, the esters comprise between 60 and 70% by weight propylene glycol monocaprylate and between 30 and 40% by weight propylene glycol dicaprylate, relative to the total weight of esters.

The esters may be present in the formulation in an amount of from 50 to 99%, or from 60 to 98%, or from 70 to 97%, or from 75 to 96%, or from 80 to 95%, or from 80 to 90%, or from 85 to 90% by weight of the formulation. For instance, the esters may be present in an amount of about 95%, about 94%, about 93%, about 92%, about 91%, about 90%, about 89%, about 88%, about 87%, about 86%, about 85%, about 84%, about 83% or about 82% by weight of the formulation.

The formulation may comprise 1 to 50% by weight of an oligonucleotide containing a CpG dinucleotide and having 6 to 40 nucleotides, preferably an oligonucleotide comprising SEQ ID NO:2, more preferably cobitolimod, and 50 to 99% by weight esters as herein defined. The formulation may comprise 2 to 40% by weight of an oligonucleotide containing a CpG dinucleotide and having 6 to 40 nucleotides, preferably an oligonucleotide comprising SEQ ID NO:2, more preferably cobitolimod, and 60 to 98% by weight esters as herein defined. The formulation may comprise 3 to 30% by weight of an oligonucleotide containing a CpG dinucleotide and having 6 to 40 nucleotides, preferably an oligonucleotide comprising SEQ ID NO:2, more preferably cobitolimod, and 70 to 97% by weight esters as herein defined. The formulation may comprise 4 to 25% by weight of an oligonucleotide containing a CpG dinucleotide and having 6 to 40 nucleotides, preferably an oligonucleotide comprising SEQ ID NO:2, more preferably cobitolimod, and 75 to 96% by weight esters as herein defined. The formulation may comprise 5 to 20% by weight of an oligonucleotide containing a CpG dinucleotide and having 6 to 40 nucleotides, preferably an oligonucleotide comprising SEQ ID NO:2, more preferably cobitolimod, and 80 to 95% by weight esters as herein defined. The formulation may comprise 10 to 15% by weight of an oligonucleotide containing a CpG dinucleotide and having 6 to 40 nucleotides, preferably an oligonucleotide comprising SEQ ID NO:2, more preferably cobitolimod, and 85 to 90% by weight esters as herein defined. The formulation may comprise or 11 to 14% by weight of an oligonucleotide containing a CpG dinucleotide and having 6 to 40 nucleotides, preferably an oligonucleotide comprising SEQ ID NO:2, more preferably cobitolimod, and 86 to 89% by weight esters as herein defined.

The formulation may comprise about 13% by weight of an oligonucleotide containing a CpG dinucleotide and having 6 to 40 nucleotides, preferably an oligonucleotide comprising SEQ ID NO:2, more preferably cobitolimod, and 87% by weight esters as herein defined. The formulation may comprise about 14% by weight of an oligonucleotide containing a CpG dinucleotide and having 6 to 40 nucleotides, preferably an oligonucleotide comprising SEQ ID NO:2, more preferably cobitolimod, and 86% by weight esters as herein defined.

The formulation of the present invention preferably comprises 11 to 14% by weight of an oligonucleotide containing a CpG dinucleotide and having 6 to 40 nucleotides, preferably an oligonucleotide comprising SEQ ID NO:2, more preferably cobitolimod, and 86 to 89% by weight esters as herein defined.

A commercially available example of suitable ester comprising a combination of both propylene glycol monocaprylate and propylene glycol dicaprylate is Capryol PGMC manufactured by Gattefosse.

The formulation may further comprise a gelling agent. The gelling agent may be hydroxypropyl methylcellulose (HPMC).

The formulation may comprise, consist essentially of or consist of an oligonucleotide containing a CpG dinucleotide and having 6 to 40 nucleotides, preferably an oligonucleotide comprising SEQ ID NO:2, more preferably cobitolimod, esters as herein defined and the gelling agent.

A commercially available example of a suitable high viscosity HPMC gelling agent is Methocel K100M manufactured by Dow Pharma Solutions.

The gelling agent may be present in the formulation an amount of from 1 to 20% by weight, or from 2 to 15% by weight, from 3 to 10% by weight or from about 4 to 8% by weight. For example, the gelling agent may be present in an amount of from about 4 to 5% by weight, for example about 5% by weight. Addition of a gelling agent, for example HPMC, increases release time whilst still providing a workable product.

For instance, the formulation may comprise 5 to 20% by weight of an oligonucleotide containing a CpG dinucleotide and having 6 to 40 nucleotides, preferably an oligonucleotide comprising SEQ ID NO:2, more preferably cobitolimod, 1 to 10% by weight HPMC and 70 to 94% by weight esters as herein defined. The formulation may comprise 10 to 15% by weight of an oligonucleotide containing a CpG dinucleotide and having 6 to 40 nucleotides, preferably an oligonucleotide comprising SEQ ID NO:2, more preferably cobitolimod, 3 to 7% by weight HPMC and 78 to 87% by weight esters as herein defined. The formulation may comprise about 11.5% by weight of an oligonucleotide containing a CpG dinucleotide and having 6 to 40 nucleotides, preferably an oligonucleotide comprising SEQ ID NO:2, more preferably cobitolimod, about 5% by weight HPMC and about 83.5% by weight propylene glycol caprylate esters.

The formulation may further comprise an antioxidant. A suitable antioxidant is butylated hydroxytoluene (BHT). The formulation may comprise, consist essentially of or consist of an oligonucleotide containing a CpG dinucleotide and having 6 to 40 nucleotides, preferably an oligonucleotide comprising SEQ ID NO:2, more preferably cobitolimod, esters as herein defined, a gelling agent and an antioxidant. The gelling agent may be HPMC. Therefore, the formulation may comprise, consist essentially of or consist of an oligonucleotide containing a CpG dinucleotide and having 6 to 40 nucleotides, preferably an oligonucleotide comprising SEQ ID NO:2, more preferably cobitolimod, esters as herein defined, HPMC and butylated hydroxytolune. Including an antioxidant helps to improve chemical stability of the base formulation over time.

The antioxidant may be present in the formulation an amount of 0.01 to 2% by weight, 0.05 to 1% by weight, 0.075 to 0.5% by weight or about 0.1% by weight.

For example, the formulation may comprise from 5 to 20% by weight of an oligonucleotide containing a CpG dinucleotide and having 6 to 40 nucleotides, preferably an oligonucleotide comprising SEQ ID NO:2, more preferably cobitolimod, from 1 to 20% by weight HPMC, from 0.01 to 2% by weight butylated hydroxytolune and from 58 to 94% esters as herein defined. The formulation may comprise from 10 to 15% by weight of an oligonucleotide containing a CpG dinucleotide and having 6 to 40 nucleotides, preferably an oligonucleotide comprising SEQ ID NO:2, more preferably cobitolimod, from 3 to 10% by weight HPMC, from 0.075 to 0.5% by weight butylated hydroxytolune and from 75 to 87% esters as herein defined.

The formulation may comprise about 11.5% by weight of an oligonucleotide containing a CpG dinucleotide and having 6 to 40 nucleotides, preferably an oligonucleotide comprising SEQ ID NO:2, more preferably cobitolimod, about 5% HPMC by weight, about 83.5% propylene glycol caprylate esters by weight and about 0.1% butylated hydroxytoluene by weight.

The formulation may further comprise a pH buffer. Thus, the formulation may comprise, consist essentially of or consist of an oligonucleotide containing a CpG dinucleotide and having 6 to 40 nucleotides, preferably an oligonucleotide comprising SEQ ID NO:2, more preferably cobitolimod, esters as herein defined, a gelling agent, an antioxidant and a pH buffer. Including a pH buffer helps to improve chemical stability of the base formulation over time.

The pH buffer may be tromethamine. The gelling agent may be a high molecular weight HPMC such as Methocel K100M. The antioxidant may be butylated hydroxytoluene. Therefore, the formulation may comprise, consist essentially of or consist of an oligonucleotide containing a CpG dinucleotide and having 6 to 40 nucleotides, preferably an oligonucleotide comprising SEQ ID NO:2, more preferably cobitolimod, esters as herein defined, HPMC, butylated hydroxytolune and tromethamine.

The pH buffer may be present in the formulation an amount of 0.05 to 5% by weight, from 0.1 to 4% by weight, from 0.1 to 3% by weight, from 0.1 to 2% by weight or from 0.1 to 1% by weight. The pH buffer may be present in the formulation in an amount from 0.1 to 0.5% by weight. The pH buffer may be present in the formulation in an amount of about 0.1% by weight, 0.2% by weight, 0.3% by weight or 0.4% by weight.

For example, the formulation may comprise from 5 to 20% by weight of an oligonucleotide containing a CpG dinucleotide and having 6 to 40 nucleotides, preferably an oligonucleotide comprising SEQ ID NO:2, more preferably cobitolimod, from 1 to 20% by weight HPMC, from 0.01 to 2% by weight butylated hydroxytoluene, from 0.05 to 5% by weight tromethamine and from 53 to 94% esters as herein defined. The formulation may comprise from 10 to 15% by weight of an oligonucleotide containing a CpG dinucleotide and having 6 to 40 nucleotides, preferably an oligonucleotide comprising SEQ ID NO:2, more preferably cobitolimod, from 3 to 10% by weight HPMC, from 0.075 to 0.5% by weight butylated hydroxytolune, from 0.1 to 1% by weight tromethamine and from 75 to 87% esters as herein defined. For example, the formulation may comprise about 11.5% by weight of an oligonucleotide containing a CpG dinucleotide and having 6 to 40 nucleotides, preferably an oligonucleotide comprising SEQ ID NO:2, more preferably cobitolimod, about 4.5% by weight HPMC, about 83.7% by weight propylene glycol caprylate esters, about 0.1% by weight butylated hydroxytoluene and about 0.2% by weight tromethamine.

The present invention also includes a capsule suitable for oral administration, said capsule comprising:
  a) a gelatin container, and within the container
  b) a formulation as defined above.
The capsule may further comprise:
  c) a coating on the exterior surface of the container.

Typically, the coating comprises a first polymer and/or a second polymer.

The first polymer is typically a low pH polymer and the second polymer is typically a high pH polymer. The first polymer typically dissolves in phosphate buffer solution at a pH of greater than or equal to pH 4.5, and below pH 7, and the second polymer typically dissolves in phosphate buffer solution at a pH of greater than or equal to 6.8.

The first polymer is typically a low pH polymer i.e. a polymer that dissolves in phosphate buffer solution at pH of greater than or equal to 4.5 and below 7. The first polymer only begins to dissolve or disintegrate when the dosage form has exited the stomach and entered the small intestine.

More preferably, the first polymer dissolves at a pH of greater than or equal to 5, and even more preferably greater than 5.5. The first polymer is fully dissolved in phosphate buffer solution at a pH of less than pH 7, more preferably less than pH 6.8. By "dissolves at a pH of greater than X" means that the polymer does not dissolve and is solid below pH X, and dissolves or disintegrates at a pH of greater than X. By "dissolves at a pH of greater than X and less than Y" means that the polymer does not dissolve and is solid below pH X, and dissolves or disintegrates at a pH of greater than X, and is fully dissolved or disintegrated at a pH of Y or less than Y.

The second polymer is typically a high pH polymer i.e. a polymer that dissolves in a phosphate buffer solution at pH of greater than 6.8. The second polymer therefore only begins to dissolve, if at all, when the dosage form has reached the distal intestinal region. More preferably, the second polymer dissolves at a pH of greater than or equal to 7.0, or may dissolve at a pH of greater than 7.2.

Typically, the coating comprises the first polymer in an amount of from 15% to 50% by weight of the coating on a dry coating basis. Typically, the coating comprises the second polymer in an amount of from 15% to 50% by weight of the coating on a dry coating basis.

The first polymer may be poly(methacrylic acid-co-ethyl acrylate) 1:1. The first polymer may be soluble above pH 5.5, i.e. the first polymer dissolves above pH 5.5. The first polymer may have a glass transition temperature between 91 and 101° C. The first polymer may have a molecular weight of between 250,000 and 500,000 g/mol, or between 275,000 and 400,000 g/mol, or between 300,000 and 350,000 g/mol, preferably about 320,000 g/mol.

For example, the first polymer may be poly(methacrylic acid-co-ethyl acrylate) 1:1 which is soluble above pH 5.5, and which has a glass transition temperature between 91 and 101° C. and has a molecular weight of about 320,000 g/mol.

A commercial example of a polymer suitable as the first polymer is Eudragit® L 30 D-55 Copolymer manufactured by Evonik.

The second polymer may be poly(methyl acrylate-co-methyl methacrylate-co-methacrylic acid) 7:3:1.

The second polymer may be soluble above pH 7, i.e. the first polymer dissolves above pH 7. The second polymer may have a glass transition temperature between 38 and 48° C. The second polymer may have a molecular weight of between 150,000 and 400,000 g/mol, or between 200,000 and 350,000 g/mol, or between 250,000 and 300,000 g/mol, preferably about 280,000 g/mol.

For example, the second polymer may be poly(methyl acrylate-co-methyl methacrylate-co-methacrylic acid) 7:3:1 which is soluble above pH 7, and which has a glass transition temperature between 38 and 48° C. and has a molecular weight of about 280,000 g/mol.

A commercial example of a polymer suitable as the second polymer is Eudragit® FS 30D Copolymer manufactured by Evonik.

Therefore typically the coating may comprise both poly(methacrylic acid-co-ethyl acrylate) 1:1 as the first polymer and poly(methyl acrylate-co-methyl methacrylate-co-methacrylic acid) 7:3:1 as the second polymer.

The poly(methacrylic acid-co-ethyl acrylate) 1:1 and poly (methyl acrylate-co-methyl methacrylate-co-methacrylic acid) 7:3:1 may be present in a weight ratio of from 5:1 to 1:5, or from 2:1 to 1:4, or from 1:1 to 1:3. The weight ratio of poly(methacrylic acid-co-ethyl acrylate) 1:1 and poly (methyl acrylate-co-methyl methacrylate-co-methacrylic acid) 7:3:1 may be about 1:1, about 1:2 or about 1:3.

Typically, the coating may comprise a first polymer which is soluble above pH 5.5 and a second polymer which is soluble above pH 7. The first polymer may have a glass transition temperature between 91 and 101° C. and the second polymer may have a glass transition temperature between 38 and 48° C.

The first polymer may have a molecular weight of from 250,000 to 500,000 g/mol and the second polymer may have a molecular weight of from 150,000 to 400,000 g/mol. The first polymer may have a molecular weight of from 275,000 to 400,000 g/mol and the second polymer may have a molecular weight of from 200,000 to 350,000 g/mol. The first polymer may have a molecular weight of from 300,000 to 350,000 g/mol and the second polymer may have a molecular weight of from 250,000 to 300,000 g/mol. Preferably, the first polymer has a molecular weight of about 320,000 g/mol and the second polymer has a molecular weight of about 280,000 g/mol.

For example, the coating may comprise a first polymer which is poly(methacrylic acid-co-ethyl acrylate) 1:1, and is soluble above pH 5.5, and has a glass transition temperature between 91 and 101° C. and has a molecular weight of about 320,000 g/mol and a second polymer which is poly(methyl acrylate-co-methyl methacrylate-co-methacrylic acid) 7:3:1 and is soluble above pH 7, and has a glass transition temperature between 38 and 48° C. and has a molecular weight of about 280,000 g/mol in a weight ratio of about 1:1.

For example, the coating may comprise a first polymer which is poly(methacrylic acid-co-ethyl acrylate) 1:1, and is soluble above pH 5.5, and has a glass transition temperature between 91 and 101° C. and has a molecular weight of about 320,000 g/mol and a second polymer which is poly(methyl acrylate-co-methyl methacrylate-co-methacrylic acid) 7:3:1 and is soluble above pH 7, and has a glass transition temperature between 38 and 48° C. and has a molecular weight of about 280,000 g/mol in a weight ratio of about 1:3.

The coating on the exterior surface of the gelatin container can be obtainable by coating the capsule in a coating solution, said coating solution comprising a first polymer and a second polymer as defined above.

The capsules may be cured following coating. The capsules may be coated using a fluid bed coating machine. The capsules may be left to cure at room temperature for a period of 1 to 24 hours, or from 3 to 18 hours, or from 6 to 12 hours, or for about 8 hours.

The coating solution may further comprise talc, triethyl citrate and water. In this case, the coating solution may comprise from 5 to 40% by weight poly(methacrylic acid-co-ethyl acrylate) 1:1, from 5 to 40% by weight poly(methyl acrylate-co-methyl methacrylate-co-methacrylic acid) 7:3:1, from 1 to 10% by weight talc, from 0.5 to 5% triethyl citrate and from 8.5 to 88.5% by weight water. The coating solution may comprise from 15 to 20% by weight poly(methacrylic acid-co-ethyl acrylate) 1:1, from 15 to 20% by weight poly(methyl acrylate-co-methyl methacrylate-co-methacrylic acid) 7:3:1, from 1 to 10% by weight talc, from 0.5 to 5% by weight triethyl citrate and from 45 to 68.5% by weight water. For instance, the coating solution may comprise about 21% by weight poly(methacrylic acid-co-ethyl acrylate) 1:1, about 21% by weight poly(methyl acrylate-co-methyl methacrylate-co-methacrylic acid) 7:3:1, about 5.5% by weight talc, about 2% by weight triethyl citrate and about 51% by weight water.

The coating solution may comprise from 5 to 15% by weight poly(methacrylic acid-co-ethyl acrylate) 1:1, from 20 to 40% by weight poly(methyl acrylate-co-methyl methacrylate-co-methacrylic acid) 7:3:1, from 1 to 10% by weight talc, from 0.5 to 5% triethyl citrate and from 30 to 73.5% by weight water. For instance, the coating solution may comprise about 10% by weight poly(methacrylic acid-co-ethyl acrylate) 1:1, about 30% by weight poly(methyl acrylate-co-methyl methacrylate-co-methacrylic acid) 7:3:1, about 5.5% by weight talc, about 2% triethyl citrate and about 51% by weight water.

In a preferred aspect, the present invention also provides a capsule suitable for oral administration, said capsule comprising:

a) a gelatin container, and within the container b) a formulation, and c) a coating on the exterior surface of the container, wherein the formulation comprises about 11.5% cobitolimod by weight, about 4.5% high molecular weight hydroxypropyl methylcellulose by weight, about 83.7% propylene glycol caprylate esters by weight, about 0.1% butyl hydroxytoluene by weight and about 0.2% tromethamine by weight; and wherein the coating comprises poly (methacrylic acid-co-ethyl acrylate) 1:1 and poly(methyl acrylate-co-methyl methacrylate-co-methacrylic acid) 7:3:1 in a ratio of about 1:1.

In a preferred aspect, the present invention also provides a capsule suitable for oral administration, said capsule comprising:

a) a gelatin container, and within the container b) a formulation, and c) a coating on the exterior surface of the container, wherein the formulation comprises about 11.5% cobitolimod by weight, about 4.5% high molecular weight hydroxypropyl methylcellulose by weight, about 83.7% propylene glycol caprylate esters by weight, about 0.1% butyl hydroxytoluene by weight and about 0.2% tromethamine by weight; and wherein the coating comprises poly (methacrylic acid-co-ethyl acrylate) 1:1 and poly(methyl acrylate-co-methyl methacrylate-co-methacrylic acid) 7:3:1 in a ratio of about 1:3.

In a preferred aspect, the present invention also provides a capsule suitable for oral administration, said capsule comprising:

a) a gelatin container, and within the container b) a formulation, and c) a coating on the exterior surface of the container, wherein the formulation comprises about 11.5% cobitolimod by weight, about 4.5% high molecular weight hydroxypropyl methylcellulose by weight, about 83.7% propylene glycol caprylate esters by weight, about 0.1% butyl hydroxytoluene by weight and about 0.2% tromethamine by weight; and wherein the coating is obtainable by coating the capsule in a coating solution, said coating solution comprising about 21% by weight poly(methacrylic acid-co-ethyl acrylate) 1:1, about 21% by weight poly (methyl acrylate-co-methyl methacrylate-co-methacrylic acid) 7:3:1, about 5.5% by weight talc, about 2% by weight triethyl citrate and about 51% by weight water.

In a preferred aspect, the present invention also provides a capsule suitable for oral administration, said capsule comprising:

a) a gelatin container, and within the container
b) a formulation, and
c) a coating on the exterior surface of the container,
wherein the formulation comprises about 11.5% cobitolimod by weight, about 4.5% high molecular weight hydroxypropyl methylcellulose by weight, about 83.7% propylene glycol caprylate esters by weight, about 0.1% butyl hydroxytoluene by weight and about 0.2% tromethamine by weight; and wherein the coating is obtainable by coating the capsule in a coating solution, said coating solution comprising about 10% by weight poly(methacrylic acid-co-ethyl acrylate) 1:1, about 30% by weight poly (methyl acrylate-co-methyl methacrylate-co-methacrylic acid) 7:3:1, about 5.5% by weight talc, about 2% triethyl citrate and about 51% by weight water.

The capsule of the present invention may be configured to release the oligonucleotide containing a CpG dinucleotide and having 6 to 40 nucleotides when exposed to conditions of a specific pH or range of pHs, corresponding to the pH of a certain area in the gastrointestinal tract, by varying the ratio of the first to second polymer in the coating.

For instance, the pH of the ileo-cecal junction is around pH 6.5 to 7.5. It is important to recognise the pH variability along the GI tract, especially in the diseased state. For example, if a coating that dissolves at pH>7.0 is applied, there is a risk that the GI tract pH would never reach the minimal value, thereby resulting in non-release of the active. This issue is often reported in some of the colon targeted drug delivery system. To overcome the problem, the coating composition of this invention is designed to include an amount of enteric polymer that dissolves at a pH lower than the target. Along with the inclusion of a controlled release mechanism in the core formulation, a "lag" time is created to delay the onset of drug release to minimise any early release as well as no release. Typically, the capsule of the present invention is configured to release the oligonucleotide containing a CpG dinucleotide and having 6 to 40 nucleotides, preferably cobitolimod, when exposed to conditions of pH 6.5 to 7.5, i.e. the onset of oligonucleotide release is between pH 6.5 to 7.5. This corresponds the pH of the ileo-cecal junction and allows the oligonucleotide to be targeted to the colon. Therefore, the capsule of the present invention, when administered orally to a subject, may be configured to commence the release of the oligonucleotide at the ileo-cecal junction. This allows the oligonucleotide to be targeted to the colon, thereby allowing targeted treatment of an inflammatory bowel disease affecting the colon, in particular ulcerative colitis or Crohn's disease. Typically, the capsule is configured to release the oligonucleotide containing a CpG dinucleotide and having 6 to 40 nucleotides, preferably cobitolimod, when exposed to conditions of pH 6.5 to 7.5 over a period of greater than 2 hours, preferably, a period of from 3 to 18 hours, and more preferably a period of from 5 to 12 hours.

The pH of the ileum (small intestine) is around pH 5.5. Alternatively, the capsule of the present invention is configured to release the oligonucleotide containing a CpG dinucleotide and having 6 to 40 nucleotides, preferably cobitolimod, when exposed to conditions of pH 5.5 to 6, i.e the onset of oligonucleotide release is between pH 5.5 and 6. This corresponds the pH of the ileum and allows the oligonucleotide to be targeted to the ileum. Therefore, the capsule of the present invention, when administered orally to a subject, may be configured to release the oligonucleotide in the ileum. This allows the oligonucleotide to be targeted to the ileum, thereby allowing targeted treatment of an inflammatory bowel disease affecting the ileum, in particular Crohn's disease.

The present invention also relates to a formulation or a capsule as described above for use in the treatment of an inflammatory bowel disease in a subject, preferably ulcerative colitis or Crohn's disease.

The formulation or capsule for use as described above may release the oligonucleotide as defined above at the ileo-cecal junction. The formulation or capsule for use as described above may release the oligonucleotide as defined above at pH 6.5 to 7.5, preferably at pH 6.5 to 6.8.

The formulation or capsule for use as described above may release the oligonucleotide as defined above in the ileum. The formulation or capsule for use as described above may release the oligonucleotide as defined above at pH 5.5 to 6.

As used herein, the term "subject" refers to a human subject/patient. The terms "subject" and "patient" are used interchangeably herein.

As used herein, the term inflammatory bowel disease (IBD) refers to a group of inflammatory conditions of the colon and the gastrointestinal tract. The major types of IBD are ulcerative colitis (UC) and Crohn's disease. The main difference between UC and Crohn's disease is the location and nature of the inflammatory changes. Crohn's disease can affect any part of the gastrointestinal tract, from mouth to anus, while UC is restricted to the colon and the rectum. In some cases, a definitive diagnosis of either Crohn's disease or UC cannot be made due to idiosyncrasies in the presentation. In these cases a diagnosis of indeterminate colitis may be made. Other forms of IBD include, but are not limited to, collagenous colitis, lymphocytic colitis, ischaemic colitis, diversion colitis, Behçet's disease and indeterminate colitis.

Typically, the inflammatory bowel disease is ulcerative colitis (UC) or Crohn's disease.

The disease ulcerative colitis (UC) is well known to one skilled in the art. Ulcerative colitis treated in accordance with the present invention may involve treatment of ulcerative proctitis, distal or left sided colitis, extensive colitis, pancolitis and pouchitis.

Patients with UC typically present with a spectrum of disease severity ranging from remission to severely active. Clinical assessment can be used to classify UC patients into 4 disease activity subgroups as defined in D'Haens, Gastroenterology 2007; 132: 763-786, the entirety of which is incorporated herein by reference: (1) remission (≤2 or 3 stools/day, without the presence of blood and/or pus in the stools, with no systemic symptoms); (2) mildly active disease (3 or 4 stools/day and/or presence of blood and/or pus in the stools less than daily, with no systemic symptoms of fever or weight loss); (3) moderately active disease (>4 stools/day and/or daily presence of blood and/or pus) with minimal systemic symptoms; and (4) severely active disease (>6 bloody stools/day, and evidence of toxicity, as demonstrated by fever, tachycardia, anemia, or an erythrocyte sedimentation rate ESR).

Typically, the patient is suffering from moderate to severe UC. Preferably, the patient is suffering from moderate to severe UC as defined above.

As used herein, the words "treatment" and "treating" are to be understood as embracing treatment and/or amelioration and/or prevention of or reduction in aggravation/worsening of symptoms of a disease or condition as well as treatment of the cause of the disease or condition, and may include reversing, reducing, or arresting the symptoms, clinical signs, and underlying pathology of a condition in a manner to improve or stabilise a subject's condition.

In particular in the context of ulcerative colitis, "treating" typically refers to inducing response or remission in a patient having active ulcerative colitis. Thus, typically, the oligonucleotide is for inducing response or remission of active ulcerative colitis in a patient. Inducing response means improving the condition of a patient by e.g. reducing and/or arresting the symptoms and clinical signs of the active disease. Inducing remission means transitioning a patient from a state where they are considered to be in an active stage of the disease to a state where they are considered to be in remission.

Induction of response or remission in UC patients is typically assessed by one or more of endoscopy, histology, patient recorded outcomes and quality of life outcomes. Thus, reference to induction of response or remission includes induction of one or more of endoscopic remission, endoscopic response, histological remission, histological response, response or remission as determined by physician or by patient recorded outcomes, and response or remission as determined by quality of life. This can typically be assessed by reference to one or more standard indices.

Typically, ulcerative colitis is chronic active ulcerative colitis.

As used herein, the term "chronic active ulcerative colitis" refers to patients with ulcerative colitis that is both active and chronic. Active ulcerative colitis is typically as defined herein, i.e. the patient is not in remission. Chronic ulcerative colitis refers to a disease characterized by a chronic inflammation of the rectal and colonic mucosa.

Preferably, reference herein to "treating" refers to inducing response or remission in a patient having chronic active ulcerative colitis. Thus, typically, the oligonucleotide is for inducing response or remission of chronic active ulcerative colitis in a patient.

Induction of response or remission in UC patients may be determined in accordance with one or more standard disease indices. Typical disease indices include but not limited to the ones mentioned below; (i) disease activity determined by clinical and biochemical disease activity, (ii) disease activity determined by endoscopic disease activity, (iii) disease activity determined by composite clinical and endoscopic disease activity indices, (iv) quality of life, (v) histologic disease activity. These indices are discussed in D'Haens (ibid).

Indices based on disease activity determined by clinical and biochemical disease activity include the Truelove and Witts Severity Index; Powell-Tuck (St. Mark's) Index; Clinical Activity (Rachmilewitz) Index; Activity (Seo) Index; Physician Global Assessment; Lichtiger (Modified Truelove and Witts Severity) Index; Investigators Global Evaluation; Simple Clinical Colitis Activity Index; Improvement Based on Individual Symptom Scores; Ulcerative Colitis Clinical Score; and Patient-defined remission. These indices are discussed in D'Haens (ibid).

Indices based on disease activity determined by endoscopic disease activity include the Truelove and Witts Sigmoidoscopic Assessment; Baron score; Powell-Tuck Sigmoidoscopic Assessment; Endoscopic (Rachmilewitz Endoscopic) Index; Sigmoidoscopic Index; Sigmoidoscopic Inflammation Grade Score; Mayo Score Flexible Proctosigmoidoscopy Assessment; Sutherland Mucosal Appearance Assessment; and Modified Baron Score. These indices are discussed in D'Haens (ibid).

Indices based on disease activity determined by composite clinical and endoscopic disease activity indices include the Mayo Score (Mayo Clinic Score/Disease Activity Index); Modified Mayo Score and Sutherland Index (Disease Activity Index/UC Disease Activity Index). Mayo Score and Sutherland Index are discussed in D'Haens (ibid).

Indices based on quality of life include the Rating Form of IBD Patient Concerns; and the Inflammatory Bowel Disease Questionnaire (IBDQ). These indices are discussed in D'Haens (ibid).

Indices based on histologic disease activity include those discussed in D'Haens (ibid) such as Geboes Index and Riley Index and further indices such as Nancy Index and Robarts Index.

Preferred indices for assessing UC patients include the Clinical Activity (Rachmilewitz) Index, Mayo Score and Modified Mayo Score.

The Clinical Activity (Rachmilewitz) Index is an index taking into account 7 variables: number of stools, blood in stools, investigator's global assessment of symptomatic state, abdominal pain or cramps, temperature due to colitis, extraintestinal manifestations, and laboratory findings. This is discussed further in D'Haens (ibid) and Rachmilewitz D., BMJ 1989; 298: 82-86, the entirety of which is incorporated herein by reference. Determination of the Clinical Activity (Rachmilewitz) Index produces a score for a patient ranging from 0 to 29 points (higher scores meaning more severe disease).

Clinical remission may be considered as a Clinical Activity (Rachmilewitz) Index score ≤4 points. Response as determined by the Clinical Activity (Rachmilewitz) Index means the patient has a lower score after treatment than before treatment.

The Mayo Score is an index taking into account 4 items: stool frequency, rectal bleeding, findings of lower GI endoscopy, and Physician's Global Assessment (PGA). This is discussed further in D'Haens (ibid) and Schroeder K W et al, N Engl J Med 1987; 317: 1625-1629, the entirety of which is incorporated herein by reference. Determination of the Mayo Score produces a score ranging from 0 to 12 points (higher scores meaning more severe disease). In addition to the four specific items, a patient's functional assessment is also measured that is not meant to be included in the 12-point index calculation but should be used as a measure of general well-being when determining the PGA score.

Mayo scoring for each of the 4 items is determined as set out in the Table below.

| Score | Stool frequency[b] | Rectal Bleeding[c] | Physician's global assessment[d] | Colonoscopy/sigmoidoscopy finding |
|---|---|---|---|---|
| 0 | Normal number of stools for this patient | No blood seen | Normal or no disease | Normal or inactive disease |
| 1 | 1 to 2 stools more than normal | Streaks of blood with stool less than half the time | Mild disease | Mild disease (erythema, decreased vascular pattern, mild friability) |
| 2 | 3 to 4 stools more than normal | Obvious blood with stool most of the time | Moderate disease | Moderate disease (marked erythema, lack of vascular pattern, friability, erosions) |

| Score | Stool frequency[b] | Rectal Bleeding[c] | Physician's global assessment[d] | Colonoscopy/ sigmoidoscopy finding |
|---|---|---|---|---|
| 3 | 5 or more stools more than normal | Blood alone passed | Severe disease | Severe disease (spontaneous bleeding, ulceration) |

[b]Each patient serves as his or her own control to establish the degree of abnormality of the stool frequency.
[c]The daily bleeding score represents the most severe day of bleeding
[d]The physician's global assessment acknowledges the 3 other criteria, the patient's daily record of abdominal discomfort and general sense of well-being, and other observations, such as physical findings and the patient's performance status.

Remission according to the Mayo Score may be defined as complete resolution of (1) stool frequency (normal stool frequency), (2) rectal bleeding (no rectal bleeding), (3) patient's functional assessment score (generally well), (4) endoscopy findings (normal), and a PGA score of 0. Response as determined by Mayo Score typically requires improvement (a minimum 1-point decrease from baseline) in the PGA score and improvement in at least one other clinical assessment (stool frequency, rectal bleeding, patient's functional assessment, endoscopy findings) and no worsening in any other clinical assessment.

Alternatively, clinical remission may be defined as a Mayo Score of 0 and clinical improvement (response) as a decrease from baseline in the Mayo Score ≥3 points.

Alternatively, clinical remission may be defined as a Mayo Score of 0 and clinical improvement (response) as a decrease from baseline in the Mayo Score ≥3 points (or a decrease of ≥2 points if the baseline Mayo Score was ≤3 points).

Alternatively, remission as determined by Mayo Score may be defined as requiring subscores of 0 for both sigmoidoscopy and rectal bleeding and a score of 0 or 1 for stool frequency and PGA subscores. Response may be defined as a decrease from baseline in the Mayo Score ≥3 points; clinical response may be defined as a decrease from baseline in the Mayo Score (without the endoscopy subscore, also known as a Partial Mayo Score) ≥2 points, and endoscopic response may be defined as a decrease from baseline in the endoscopic subscore ≥1 point.

Alternatively, clinical remission may be defined as a total Mayo score of ≤2 points with no individual subscore ≥1 point, clinical response may be defined as a decrease from baseline in the total Mayo score ≥3 points and ≥30% and a decrease in the rectal bleeding subscore ≥1 point or an absolute rectal bleeding subscore of 0 or 1, and mucosal healing may be defined as an absolute endoscopy subscore of 0 or 1.

Typically, patients having active ulcerative colitis have a Mayo Score >2. Patients who are in a remission phase of ulcerative colitis typically have a Mayo Score ≤2.

Modified Mayo Score is related to the Mayo Score, which is defined above. Modified Mayo Score differs from Mayo Score in that the Colonoscopy/sigmoidoscopy scoring takes less account of friability. Thus, the scoring table for the Modified Mayo Score is as set out below.

| Score | Stool frequency[b] | Rectal Bleeding[c] | Physician's global assessment[d] | Colonoscopy/ sigmoidoscopy finding |
|---|---|---|---|---|
| 0 | Normal number of stools for this patient | No blood seen | Normal or no disease | Normal or inactive disease |
| 1 | 1 to 2 stools more than normal | Streaks of blood with stool less than half the time | Mild disease | Mild disease (erythema, decreased vascular pattern) |
| 2 | 3 to 4 stools more than normal | Obvious blood with stool most of the time | Moderate disease | Moderate disease (marked erythema, lack of vascular pattern, friability, erosions) |
| 3 | 5 or more stools more than normal | Blood alone passed | Severe disease | Severe disease (spontaneous bleeding, ulceration) |

[b]Each patient serves as his or her own control to establish the degree of abnormality of the stool frequency.
[c]The daily bleeding score represents the most severe day of bleeding
[d]The physician's global assessment acknowledges the 3 other criteria, the patient's daily record of abdominal discomfort and general sense of well-being, and other observations, such as physical findings and the patient's performance status.

Remission and response values for the Modified Mayo Score are as set out above for the Mayo Score. Modified Mayo Score is typically assessed in accordance with the FDA's draft guidance document "Ulcerative Colitis: Clinical Trial Endpoints Guidance for Industry" found at http://www.fda.gov/downloads/Drugs/GuidanceCompliance-RegulatoryInformation/Guidan ces/UCM515143.pdf Alternatively, Modified Mayo Score may differ from Mayo Score in that the Colonoscopy/sigmoidoscopy scoring takes less account of friability and also in that Physician's Global Assessment is not determinative. Thus, the scoring table for the Modified Mayo Score may also be as follows.

| Score | Stool frequency[b] | Rectal Bleeding[c] | Colonoscopy/sigmoidoscopy finding |
|---|---|---|---|
| 0 | Normal number of stools for this patient | No blood seen | Normal or inactive disease |
| 1 | 1 to 2 stools more than normal | Streaks of blood with stool less than half the time | Mild disease (erythema, decreased vascular pattern) |
| 2 | 3 to 4 stools more than normal | Obvious blood with stool most of the time | Moderate disease (marked erythema, lack of vascular pattern, friability, erosions) |
| 3 | 5 or more stools more than normal | Blood alone passed | Severe disease (spontaneous bleeding, ulceration) |

[b]Each patient serves as his or her own control to establish the degree of abnormality of the stool frequency.
[c]The daily bleeding score represents the most severe day of bleeding Remission and response values for this alternative Modified Mayo Score are typically as set out above for the Mayo Score. Alternatively, remission may be defined in accordance with this alternative Modified Mayo Score by subscores of i) rectal bleeding of 0, ii) stool frequency of 0 or 1 (with at least one point decrease from Baseline, Week 0), and iii) endoscopy score of 0 or 1 (excluding friability).

Induction of remission of UC may be in accordance with the criteria set out in S. P. L. Travis, Aliment Pharmacol Ther 2011; 34: 113-124, the entirety of which is incorporated herein by reference, i.e. complete cessation of rectal bleeding, urgency and increased stool frequency, preferably confirmed by endoscopic mucosal healing.

Alternatively, induction of response or remission may be in accordance with the criteria set out in E. F. Stange, Journal of Crohn's and Colitis (2008) 2, 1-23; S. P. L. Travis, Journal of Crohn's and Colitis (2008) 2, 24-62; K Geboes, Gut 2000; 47: 404-409; the entirety of which are incorporated herein by reference.

Induction of response or remission in Crohn's disease patients may be determined in accordance with one or more standard disease indices. Typical indices include the Crohn's Disease Activity Index (CDAI). The CDAI is discussed in Love, "Pharmacotherapy for Moderate to Severe Inflammatory Bowel Disease: Evolving Strategies", Am J Manag Care. 2016; 22:S39-S50; Peyrin-Biroulet et al "Defining disease severity in inflammatory bowel diseases: current and future directions" Clin Gastroenterol Hepatol. 2015; pii: S1542-3565(15)00787-00789. doi: 10.1016/j.cgh.2015.06.001; and Ungar et al "Advances in the development of new biologics in inflammatory bowel disease", Annals of Gastroenterology (2016) 29, 243-248. Alternative indices for assessing Crohn's disease patients include the Harvey-Bradshaw index and the Inflammatory Bowel Disease Questionnaire.

CDAI is a composite score taking into account a large number of symptoms associated with Crohn's disease, including number of liquid or soft stools; abdominal pain; general well being; presence of complications (the presence of joint pains (arthralgia) or frank arthritis; inflammation of the iris or uveitis; presence of erythema nodosum, pyoderma gangrenosum, or aphthous ulcers; anal fissures, fistulae or abscesses; other fistulae; fever during the previous week); use of lomotil or opiates for diarrhea; presence of an abdominal mass; hematocrit value; and percentage deviation from standard weight. Clinical remission according to the CDAI is typically indicated by a score of <150.

The subject treated in accordance with the present invention is typically refractory or responds insufficiently or is intolerant to anti-inflammatory therapy and/or demonstrates or has previously demonstrated an inadequate response, loss of response, or intolerance to at least one immunomodulator, TNF-α inhibitor or anti-integrin. Thus, typically, the subject has previously received or is currently receiving anti-inflammatory therapy, preferably anti-inflammatory therapy for UC and/or immunomodulatory, TNF-α inhibitor or anti-integrin therapy, preferably such therapy for UC. Anti-inflammatory therapies for UC are discussed herein and typically include GCS, sulfasalazine and 5-ASA.

Immunomodulators, TNF-α inhibitors and anti-integrins are discussed herein and typically include azathioprine, 6-mercaptopurine and biologicals including the TNF-α inhibitors infliximab and biosimilars and derivatives thereof, golimumab and biosimilars and derivatives thereof, adalimumab and biosimilars and derivatives thereof and anti-integrins vedolizumab and biosimilars and derivatives thereof.

A refractory disease or disease that responds insufficiently to therapy is typically a disease where signs and symptoms of active disease persist despite a history of at least one course of therapy, anti-inflammatory therapy in the context of the present invention. Typically in the context of treatment of UC, signs and symptoms of active disease persist despite a history of earlier courses of anti-inflammatory therapy. A typical course of treatment with anti-inflammatory therapy for UC would be well understood by a person skilled in the art, and would typically involve a sufficient number of doses at sufficient dosage to induce remission in a typical patient.

Intolerance to therapy, anti-inflammatory therapy in the context of the present invention, means that the therapy has caused side effects in the subject that are not tolerated, e.g. that typically lead to discontinuation of therapy.

Typically, the subject has previously received or is currently receiving Aminosalicylic acid (5-ASA), preferably 5-ASA therapy for UC.

Typically, the subject has previously received or is currently receiving oral Glucocorticosteroids (GCS), preferably oral GCS therapy for UC.

Typically, the subject who is refractory or responds insufficiently or is intolerant to anti-inflammatory therapy shows or has previously shown an inadequate response to, or loss of response to (i.e. is refractory to) or intolerance of rectal, oral, and/or parenteral GCS treatment (including no GCS treatment due to earlier side effect).

Typically, the subject who is refractory or responds insufficiently or is intolerant to anti-inflammatory therapy has a history of or current status of an inadequate response (e.g. steroid refractory) to, OR steroid dependency, OR loss of response to, OR intolerance of GCS treatment. The steroids/GCS will typically have been received by the subject in the course of treating ulcerative colitis.

Steroid-refractory typically refers to a subject lacking a meaningful clinical response, i.e. showing signs and symptoms of persistently active ulcerative colitis, despite a history of at least one course of steroid treatment, for instance an induction regimen that included a dose equivalent to prednisone 40-60 mg daily over a period of 30 days for oral administration or over a period of 7 to 10 days for intravenous (IV) administration.

Steroid dependence typically refers to a patient who is either unable to reduce steroids below the equivalent of prednisolone 10 mg/d within 3 months of starting steroids, without recurrent active ulcerative colitis, or who has a relapse within 3 months of stopping steroids.

Intolerance of GCS treatment typically means the subject has experienced side effects not tolerated by the subject following GCS treatment, such as but not limited to Cushing's syndrome, osteopenia/osteoporosis, hyperglycemia, insomnia, or infection.

An inadequate response, or loss of response to an immunomodulator typically means signs and symptoms of active ulcerative colitis persist despite previous treatment with at least one immunomodulator, for instance one 8 Week regimen of oral azathioprine (≥1.5 mg/kg) or 6-mercaptopurine (≥0.75 mg/kg).

Intolerance to an immunomodulator typically means the subject has experienced nausea/vomiting, abdominal pain, pancreatitis, liver function test (LFT) abnormalities, lymphopenia, Thiopurine Methyltransferase (TPMT) genetic mutation, or infection or other side effects after receiving an immunomodulator.

An inadequate response, or loss of response to a TNF-α inhibitor means signs and symptoms of active ulcerative colitis persist despite previous treatment with at least one TNF-α inhibitor, such as 4-Week induction regimen (or doses as recommended according to the current labels) of infliximab (5 mg/kg (IV), 2 doses at least 2 weeks apart) or a biosimilar or derivative thereof; golimumab (200/100 mg (SC), 2 doses at least 2 weeks apart) or a biosimilar or derivative thereof; or adalimumab (160/80 mg (SC), 2 doses at least 2 weeks apart) or a biosimilar or derivative thereof or recurrence of symptoms during maintenance dosing following prior clinical benefit.

Intolerance to a TNF-α inhibitor means an infusion-related reaction, demyelination, congestive heart failure, infection or other side effects following receipt of a TNF-α inhibitor.

An inadequate response, or loss of response to an anti-integrin means signs and symptoms of active ulcerative colitis persist despite previous treatment with an anti-integrin, for instance at least 10 weeks regimen of vedolizumab 300 mg (IV) or a biosimilar or derivative thereof, or as recommended in the current label, or recurrence of symptoms during maintenance dosing following prior clinical benefit.

Typically, the subject has been diagnosed with left sided ulcerative colitis, i.e. distal colitis, including proctosigmoiditis.

Typically, the subject has been diagnosed with pancolitis.

Typically, said subject is elective for colectomy.

As used herein, the term "colectomy" refers to surgical resection of any extent of the large intestine (colon). Herein, colectomy includes, but is not limited to, right hemicolectomy, left hemicolectomy, extended hemicolectomy, transverse colectomy, sigmoidectomy, proctosigmoidectomy, Hartmann operation, "double-barrel" or Mikulicz colostomy, total colectomy (also known as Lane's Operation), total procto-colectomy and subtotal colectomy. As used herein, the phrase "elective for colectomy" refers to a subject who may choose to undergo the procedure of non-emergency colectomy based on physician and surgeon assessment. Subjects elective for colectomy may be, but are not limited to, subjects refractory to available therapy (for ulcerative colitis) or intolerant of available therapy (for ulcerative colitis). This differs from emergency colectomy, which is an acute intervention for subjects with acute illnesses or injuries and who require immediate medical attention. The phrase also includes subjects that are elected for colectomy.

The formulations and capsules of the present invention may be administered as monotherapy treatment for the indication or with other drug(s) as adjunct therapy for the indication, as described in more detail below. For, example the subject may receive one or more additional therapeutic agents for the treatment of an inflammatory bowel disease, typically ulcerative colitis or Crohn's disease.

In the case of adjunct (or "add-on") therapy, the drugs for use in the present invention may be administered simultaneously, separately or sequentially with the other drug(s), for example in fixed dose combination or in separate doses.

As used herein, the term "add-on" refers to administering of said oligonucleotide in addition to a current therapy or drug regime, without discontinuing the current therapy or drug regime.

Thus, the oligonucleotide may be administered as a monotherapy, or in combination with one or more additional therapeutic agents for the treatment of inflammatory bowel disease, preferably ulcerative colitis or Crohn's disease. Typically, the oligonucleotide may be administered as a monotherapy, or in combination with one or more additional therapeutic agents for the treatment of ulcerative colitis chosen from immunomodulatory drugs, anti-TNF therapy drugs or other suitable drugs for treating ulcerative colitis.

Examples of such drugs suitable for use in combination with said oligonucleotide include, but are not limited to GCS or derivatives; prednisolone, Decortin, anti-TNF or derivative; infliximab and biosimilars and derivatives thereof, adalimumab and biosimilars and derivatives thereof, golimumab and biosimilars and derivatives thereof, anti-integrin or derivatives; vedolizumab and biosimilars and derivatives thereof, natural IFN-β, thiopurine or derivatives; azathioprine, 6-mercaptopurine, 5-ASA, sulphasalazine, methotrexate, cylclosporine, tofacitinib and equivalents thereof.

Typically, the subject receiving said oligonucleotide also receives one or more other drugs chosen from GCS, Decortin, 5-ASA, azathioprine, 6-mercaptopurine, sulphasalazine, methotrexate, prednisolone and equivalents thereof or derivatives.

Preferably, the subject receiving said oligonucleotide also receives one or more other drugs chosen from GCS, 5-ASA, azathioprine, 6-mercaptopurine, sulphasalazine and methotrexate.

More preferably, the subject receiving said oligonucleotide also receives one or more other drugs chosen from oral GCS, oral 5-ASA, azathioprine, 6-mercaptopurine, and oral methotrexate.

Typically, the subject receiving said oligonucleotide also receives one or more steroid drugs, for example corticosteroids and glucocorticosteroids.

For purposes of the invention, the terms "in combination with" and "add-on" mean in the course of treating the same disease in the same patient, and include administering the oligonucleotide and one or more additional therapeutic agents in any order, including simultaneous administration, as well as temporally spaced order of up to several months apart.

Typically, the formulation or capsule is administered orally.

The invention also provides a method of treating inflammatory bowel disease, preferably ulcerative colitis or Crohn's disease, in a subject, the method comprising orally administering to said subject a formulation or capsule as defined herein.

The invention also provides the use of a formulation or a capsule as defined herein for the manufacture of a medicament for treatment of inflammatory bowel disease, preferably ulcerative colitis or Crohn's disease.

The following non-limiting Examples illustrate the invention. Throughout the Examples, the terms active pharmaceutical ingredient (API) and cobitolimod have been used interchangeably.

Example 1—Cobitolimod/Excipient Compatibility Studies 1.1 Materials

The excipients other materials used in this study are detailed in Tables 1 and 2.

TABLE 1

| Excipients used in this study | |
|---|---|
| Excipient | Manufacturer |
| Precirol AT05 | Gattefosse |
| Stereotex | Abitec |
| Geleol | Gattefosse |
| Gelucire 43/01 | Gattefosse |
| Vit E TPGS | Anta res |
| Gelucire 48/16 | Gattefosse |
| PEG 1500 | Croda |
| Tween 80 | Croda |
| Capryol PGMC | Gattefosse |
| Labra sol | Gattefosse |
| Miglyol | Cremer Oleo |

TABLE 2

Other materials used in this study.

| Material | Manufacturer |
|---|---|
| Gelatin | Gelita |
| Sterile water | Fresnius Kabi |
| Pharmacoat 603 | Shin Etsu |
| Ethanol (96% v/v) | Fisher |
| Conisnap gelatin capsules, size 1 | Capsugel |
| VCAPS Plus HPMC capsules, size 1 | Capsugel |

1.2 Cobitolimod Solubility Assessment Method

Solubility was assessed through kinetic solubility method through stepwise addition of the API to the excipients until a maximal solubility is attained.

1.3 Cobitolimod/Excipient Compatibility Study Method

The cobitolimod-containing mixes and their corresponding placebo were analysed using HPLC with UV detection at two time points: at no longer than 4 weeks after preparation and subsequent storage at 2-8° C. (T=0), and after being set down for 4 weeks at 40° C./75% relative humidity (T=4).

1.4 Capsule Shell Compatibility Method

The cobitolimod-containing mixes and the corresponding placebo mixes were filled into each type of capsule (gelatin and HPMC) to give a target concentration of 30 mg per capsule. The capsules were then banded using an appropriate banding solution, and left to dry overnight. The capsules were then leak tested in a vacuum chamber for 20 minutes and subsequently visually assessed for leaking or cracking. After inspection, the capsules were set down on stability at 40° C./75% relative humidity for 2 weeks and then once again visually checked for leaks, cracks and deformations of the capsule shell.

1.5 Cobitolimod Solubility Assessment Results

The results of the solubility assessment showed that all the mixes were suspensions at the initial 40 mg cobitolimod in 8 g excipient concentration.

Table 3 shows which binary mixes were workable at 600 mg cobitolimod in 8 g excipient concentration and which mixes were unworkable.

TABLE 3

Results of solubility assessment study at final 600 mg cobitolimod (API) in 8g excipient concentration.

| Binary mix | Observations at 600 mg/8 g concentration |
|---|---|
| Precirol AT05 + API | Very clumpy and unworkable at 600 mg API concentration |
| Stereotex + API | Fluid and workable |
| Geleol + API | Fluid and workable |
| Gelucire 43/01 + API | Fluid and workable |
| Vi t E TPGS + API | Unworkable at 400 mg API concentration |
| Gelucire 48/16 +API | Unworkable at 600 mg API concentration |
| PEG 1500 + API | Fluid and workable |
| Tween 80 + API | Unworkable at 400 mg API concentration |
| Capryol PGMC + API | Fluid and workable |
| Labrasol + API | Unworkable at 400 mg API concentration |
| Miglyol + API | Unworkable at 600 mg API concentration |

1.6 Capsule Shell Compatibility Study Results

Table 4 and Table 5 detail the five mixes that were taken forward for the capsule shell compatibility study.

TABLE 4

Capsule shell compatibility study cobitolimod (API) mixes.

Binary mix

Stereotex + API
Geleol + API
Gelucire 43/01 + API
PEG 1500 API
Capryol PGMC + API

TABLE 5

Capsule shell compatibility study placebo mixes

Placebo mix

Stereotex
Geleol
Gelucire 43/01
PEG 1500
Capryol PGMC

Table 6 details the results of the study immediately prior to set down and after the 2 week set down time point. Capryol PGMC placebo in HPMC capsules not carried forward due to the corresponding Capryol and cobitolimod in HPMC capsules having all cracks developed during the banding process. Table 7 details the results of the excipient+cobitolimod capsule immediately prior to set down and after the 2-week set down time point. The Gelucire 43/01+cobitolimod capsules showed same signs of deformation on the capsules, however this could be due to the band softening during storage at 40° C. and getting flattened against the bottom of the amber jar. The corresponding excipient only capsules showed no signs of capsule deformation. The Capryol PGMC cobitolimod containing mix were not set down in HPMC capsule due to all the capsules cracked after banding.

TABLE 6

Excipient only capsule shell compatibility study results prior to and after 2 week setdown.

Excipient only

| Capsule shell | Excipient base | Observations prior to set down | Observations after 2 weeks at 40° C./75% RH |
|---|---|---|---|
| HPMC | Sterotex | No issue | No issue |
| HPMC | Geleol | No issue | No issue |
| HPMC | Gelucire 43/01 | No issue | No issue |
| HPMC | PEG 1500 | No issue | No issue |
| Gelatin | Sterotex | No issue | No issue |
| Gelatin | Geleol | No issue | No issue |
| Gelatin | Gelucire 43/01 | No issue | No issue |
| Gelatin | PEG 1500 | No issue | No issue |
| Gelatin | Capryol PGMC | No issue | No issue |

TABLE 7

Excipient + cobitolimod (API) capsule shell compatibility study results prior to and after 2 week set down. API/Excipient binary mix

| Capsule shell | Excipient base | Observations prior to set down | Observations after 2 weeks at 40° C./75% RH |
|---|---|---|---|
| HPMC | Sterotex + API | No issue | No issue |
| HPMC | Geleol + API | No issue | No issue |
| HPMC | Gelucire 43/01 + API | No issue | No issue |
| HPMC | PEG 1500 + API | No issue | No issue |
| HPMC | Capryol PGMC + API | All 5 capsules cracked after banding and before leak testing. | NA |
| Gelatin | Sterotex API | No issue | No issue |
| Gelatin | Geleol + API | No issue | No issue |
| Gelatin | Gelucire 43/01 + API | No issue | 2 capsules showing some signs of deformation |
| Gelatin | PEG 1500 + API | No issue | No issue |
| Gelatin | Capryol PGMC + API | No issue | No issue |

1.7 Cobitolimod/Excipient Compatibility Study Results

The following mixes as detailed in Table 8 were carried forward for the cobitolimod/excipient compatibility study.

TABLE 8

Mixes carried forward for cobitolimod/excipient compatibility study. Sample

Sterotex + API
Geleol + API
Gelucire 43/01 + API
PEG 1500 + API
Capryol PGMC + API
Sterotex (placebo)
Geleol (placebo)
Gelucire 43/01 (placebo)
PEG 1500 (placebo)
Capryol PGMC (placebo)

The samples were analysed at the initial and 4 week time points for related substances and assay values and the results are reported based on area %.

FIG. 1 below shows a comparison of the cobitolimod standard compared to the 5 binary mixes prepared at the initial time point. The chromatogram shows same degradation in the Geleol and PEG 1500 mixes but there is no noticeable change between API standard and the initial time point samples for the remaining Capryol, Gelucire and Sterotex mixes.

Figure 2:
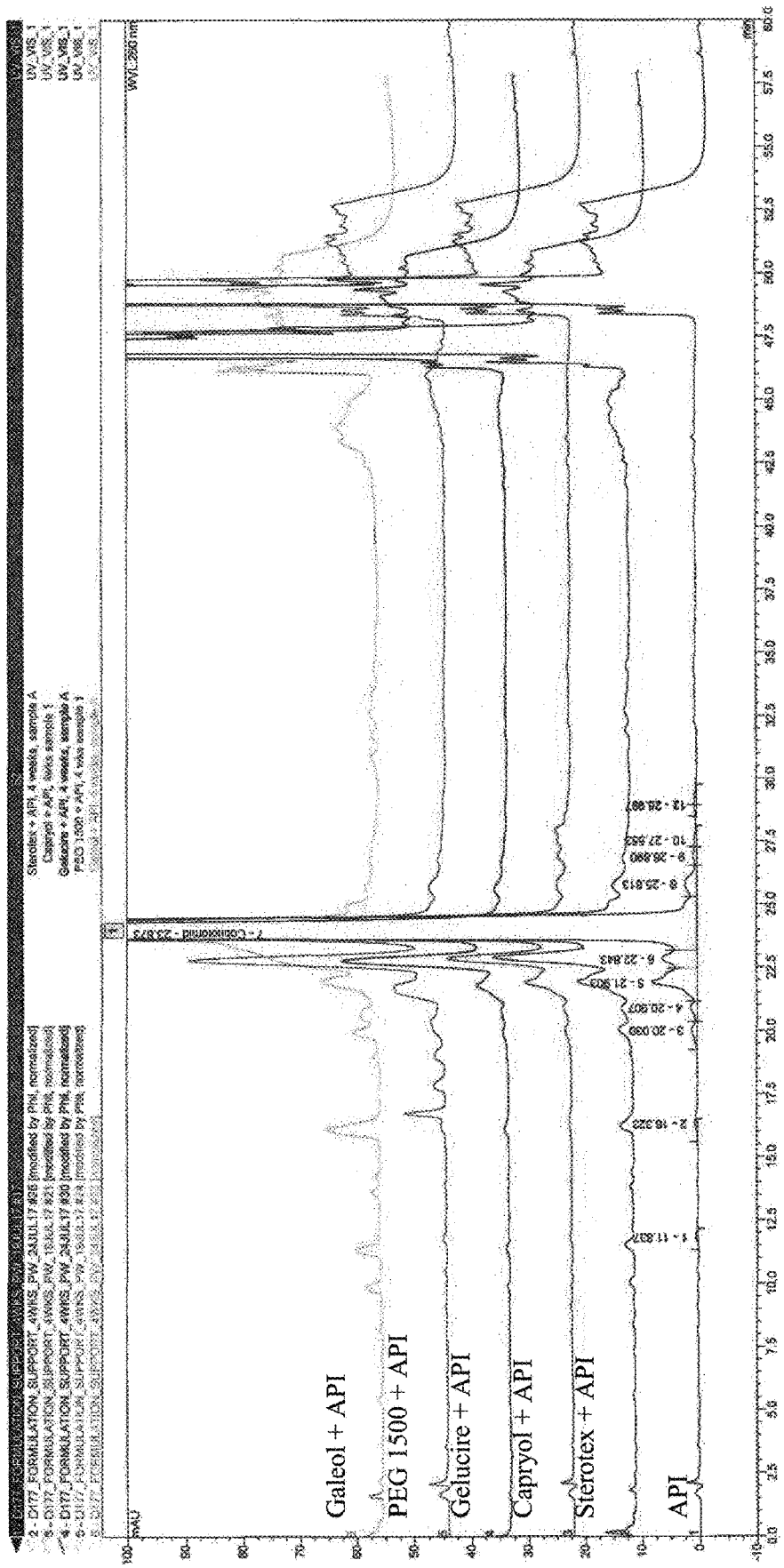
FIG. 2 shows a chromatogram comparing the cobitolimod standard to the 5 binary mixes with different excipients (Capryol, Sterotex, Gelucire, PEG 1500 and Geleol) at the 4 week time point.

FIG. 2 below shows a comparison of the cobitolimod standard compared to the 5 binary mixes at the 4 week time point. The chromatography shows there is noticeable degradation in the Sterotex, PEG 1500 and Geleol mixes and slight degradation on the Gelucire mix after 4 weeks. The Capryol mix appears to show very little if any degradation after 4 weeks.

1.8 Sterotex and Cobitolimod

The Sterotex+ cobitolimod sample showed a moderate increase in related substances (RS) of 5.5% between the initial and 4 week time points and an increase in assay of 28% (Table 9). This sample also exhibited different behaviour after the 4 week time point, with a solid pellet forming on the bottom of the vial that could not be homogenised by stirring, heating or sonication. The increase in assay values is likely due to the mix being non-uniform during sampling.

TABLE 9

Sterotex RS and assay results.

| Initial RS results (%) | 4 week RS results (%) | Change in RS results (%) | Initial assay results (%) | 4 week assay results (%) | Change in assay results (%) |
|---|---|---|---|---|---|
| 5.90 | 11.44 | +5.54 | 87 | 115 | +28 |

1.9 Geleol and Cobitolimod

The Geleol+ cobitolimod sample showed a significant increase in related substances (RS) of 13.6% between the initial and 4 week time points and a significant decrease in assay of 28% (Table 10). This sample also exhibited different behaviour after the 4 week time point, with a solid pellet forming on the bottom of the vial that could not be homogenised by stirring, heating or sonication. The decrease in assay values is highly likely to be due to the cobitolimod degradation and also due to the sample not being homogeneous at the 4 week time point.

TABLE 10

Geleol RS and assay results.

| Initial RS results (%) | 4 week RS results (%) | Change in RS results (%) | Initial assay results (%) | 4 week assay-results (%) | Change in assay-results (%) |
|---|---|---|---|---|---|
| 7.63 | 21.26 | +13.63 | 94 | 66 | −28 |

1.10 Gelucire 43/01 and Cobitolimod

The Gelucire 43/01+ cotibolimod sample showed an increase in related substances of 8.3% between the initial and 4 week time points and a significant decrease in assay of 11% (Table 11). This sample also exhibited different behaviour after the 4 week time point, with a solid pellet forming on the bottom of the vial that could not be homogenised by stirring, heating or sonication. The decrease in assay values is likely due to cotibolimod degradation and also due to the sample not being homogeneous at the 4 week time point which is also indicated by the low initial assay result.

TABLE 11

Gelucire 43/01 RS and assay results

| Initial RS results (%) | 4 week RS results (%) | Change in RS results (%) | Initial assay results (%) | 4 week assay results (%) | Change in assay results (%) |
|---|---|---|---|---|---|
| 5.76 | 14.01 | +8.25 | 70 | 59 | −11 |

1.11 PEG1500 and Cobitolimod

The PEG1500+ cobitolimod sample showed an increase in related substances of 6.6% between the initial and 4 week time points and a significant decrease in assay of 11% (see Table 12). However, no changes in dispersion characteristics are observed.

TABLE 12

PEG1S00 RS and Assay results

| Initial RS results (%) | 4 week RS results (%) | Change in RS results (%) | Initial assay results (%) | 4 week assay results (%) | Change in assay results (%) |
|---|---|---|---|---|---|
| 9.15 | 15.70 | +6.55 | 92 | 81 | −11% |

1.12 Capryol PGMC and Cobitolimod

The Capryol PGMC+ cobitolimod sample showed a slight increase of 1.8% in related substances between the initial and 4 week time points and a slight increase in the assay value of 4% (Table 13). No changes in dispersion characteristic is observed.

TABLE 13

Capryol PGMC RS and Assay results.

| Initial RS results (%) | 4 week RS results (%) | Change in RS results (%) | Initial assay results (%) | 4 week assay results (%) | Change in assay results (%) |
|---|---|---|---|---|---|
| 5.24 | 7.05 | +1.81 | 97 | 101 | +4 |

The Capryol PGMC based system had the least amount of degradation. In addition, it is worth of noting that, re-dispersibility issues were observed in the hydrophobic high melting wax systems, but not the Capryol and the PEG system suggesting this may be related to cobitolimod aggregation in the hydrophobic environment. Further work on the inclusion of a small amount of antioxidant and pH buffering material in these excipients to minimise degradation is found in Example 3.

1.13 Conclusion

All of the mixes studied provided a suspension with none showing any degree of solubility, thus the cobitolimod will be prepared as a suspension for further development.

Degradation was detected to a different extent during preparation of all suspensions. The Capryol PGMC based system had the least amount of degradation. The reasons for the apparent degradation of the cobitolimod in the cobitolimod/excipient compatibility study could be due to the cobitolimod being sensitive to oxidation as well as acid degradation and the temperatures used in the preparation of the samples. Redispersibility issues were observed in the hydrophobic high melting wax systems, but not the Capryol and the PEG systems suggesting dispersibility may be related to cobitolimod aggregation in the hydrophobic environment.

Example 2—Basic Core Formulation

Example 1 has demonstrated that Capryol PGMC was the most appropriate carrier material in terms of chemical compatibility with cobitolimod. This carrier is anticipated to release cobitolimod relatively fast and therefore addition of hydroxypropyl methyl cellulose (HPMC) is suggested. The objectives of this study were firstly to investigate the limit of cobitolimod suspension achievable in Capryol PGMC excipient to determine if sufficient cobitolimod could be suspended to reach a reasonable/suitable concentration of cobitolimod and the suspension remain workable at the increased cobitolimod loading; secondly to investigate the limit of suspendability of Methocel/HPMC in Capryol PGMC and visually assess the gel forming properties of various concentrations and compositions of HPMC in Capryol PGMC to determine the most suitable compositions and concentrations for further study; and thirdly to investigate various different cobitolimod/Capryol/HPMC compositions and concentrations for workability and visual gel forming profile.

2.1 Materials

TABLE 14

Excipient and materials list

| Material | Function | Manufacturer |
|---|---|---|
| Capryol PGMC | Excipient | Gattefosse |
| Methocel K100M (HPMC 1) | Gelling agent High viscosity | Colorcon |
| Methocel E3 (HPMC 2) | Gelling agent Low viscosity | Colorcon |

2.2 Cobitolimod Suspension Limit in Capryol Only Method

The cobitolimod suspension limit in Capryol only was assessed by repeating the steps of (i) adding the API to Capryol, (ii) spatula stirring and (iii) sonication, until the suspension became unworkable due to, for example, being too viscous, agglomerates forming that would not break down etc.

2.3 Preliminary Dispersion Testing of HPMC/Capryol Mix Method

The preliminary dispersion testing of five different ratios of the HPMC/Capryol mix was carried out using the following method: A 500 ml beaker was filled with 250 ml of Milli-Q water and placed in a water bath at 37° C. and the temperature allowed to equilibrate. 1 g of each of the five mixes prepared in Tables 15 and 16 below was added to the beaker and gently stirred by a magnetic stirrer. Two grades of HPMC were used for this study, HPMC 1 was Methocel K100M high molecular weight HPMC and HPMC 2 which was Methocel E3 low molecular weight HPMC.

Visual observations of the dispersion test results such as solution colour, particles, sedimentation, agglomerates etc were made at initial addition of sample, 5 minute, 30 minute, 1 hour, 2 hour, 4 hour, 5 hour and 24 hour time points. After the 5 hour time point stirring was stopped and the solution was allowed to settle for 24 hours.

TABLE 15

High viscosity HPMC/Excipient dispersion testing mix composition (HPMC 1 is Methocel K100M high viscosity HPMC)

| Mix | Composition Capryol/HPMC 1 | Capryol weight (g) | HPMC weight (g) | Total mix weight (g) |
|---|---|---|---|---|
| 1 Placebo | 95.0%/5.0% | 4.75 | 0.25 | 5.00 |
| 2 Placebo | 90.0%/10.0% | 4.50 | 0.50 | 5.00 |
| 3 Placebo | 85.0%/15.0% | 4.25 | 0.75 | 5.00 |

TABLE 16

High and low viscosity HPMC/Excipient dispersion testing mix composition (HPMC 1 is Methocel K100M high viscosity HPMC; HPMC 2 is Methocel E3 low viscosity HPMC)

| Mix | Composition Capryol/HPMC 1/ HPMC 2 | Capryol weight (g) | HPMC 1 weight (g) | HPMC2 weight (g) | Total mix weight (g) |
|---|---|---|---|---|---|
| 4 Placebo | 90.0%/5.0%/5.0% | 4.50 | 0.25 | 0.25 | 5.00 |
| 5 Placebo | 85.0%/10.0%/5.0% | 4.25 | 0.50 | 0.25 | 5.00 |

2.4 Cobitolimod Capryol HPMC Formulation Study

The following samples were prepared for the preliminary dispersion testing of HPMC/Capryol/cobitolimod and were assessed for workability. Two grades of HPMC were used, with 3 mixes being based on high molecular weight HPMC (Methocel K100l\4) and the remaining 2 mixes being a mix of high molecular weight HPMC 1 (Methocel K100M) and low molecular weight HPMC 2 (Methocel E3). This was to examine if the combined low and high molecular weight HPMC mixes would form a gel more rapidly than the high molecular weight HPMC 1 only mix as well as studying the effects on the workability of the formulations.

The samples were prepared by adding the API and HPMC in stepwise additions to Capryol with 15 minutes sonication at 25° C. between additions to produce a fine uniform suspension. The five samples prepared are detailed below in Tables 17 and 18.

TABLE 17

High viscosity HPMC/Excipient/cobitolimod dispersion testing mix composition (HPMC 1 is Methocel K100M high viscosity HPMC)

| Mix | Composition Capryol/HPMC1/ API | Capryol weight (g) | HPMC1 weight (g) | API weight (g) | Total mix weight (g) |
|---|---|---|---|---|---|
| 1 Active | 83.5%/5.0%/11.5% | 4.175 | 0.250 | 0.575 | 5.000 |
| 2 Active | 78.5%/10.0%/11.5% | 3.925 | 0.500 | 0.575 | 5.000 |
| 3 Active | 73.5%/15.0%/11.5% | 3.675 | 0.750 | 0.575 | 5.000 |

TABLE 18

High and low viscosity HPMC/excipient/cotibolimod dispersion testing mix composition (HPMC 1 is Methocel K100M high viscosity HPMC; HPMC 2 is Methocel E3 low viscosity HPMC)

| Mix | Composition Excipient/HPMC 1/ HPMC 2/API | Capryol weight (g) | HPMC 1 weight (g) | HPMC2 weight (g) | API weight (g) | Total mix weight (g) |
|---|---|---|---|---|---|---|
| 4 Active | 78.5%/5.0%/5.0%/ 11.5% | 3.925 | 0.250 | 0.250 | 0.575 | 5.000 |
| 5 Active | 73.5%/10.0%/5.0%/ 11.5% | 3.675 | 0.500 | 0.250 | 0.575 | 5.000 |

2.5 Cobitolimod/Capryol/HPMC Dispersion Testing Method

Preliminary dispersion testing of the HPMC/Capryol/API mixtures set out in Tables 17 and 18 above were carried out by adding the mixtures to distilled water at 37° C. under gentle stirring and recording observations at various time intervals after addition. Stirring was ceased 5 hours after addition.

2.6 Cobitolimod Limit of Suspension Study in Capryol Only Results

The results of the cobitolimod limit of suspension at 25° C. study using cobitolimod and Capryol PGMC are detailed in Table 19. The data suggests a maximum of 13-14% cobitolimod (corresponding to approx. 53 mg cobitolimod/capsule) in Capryol PGMC is the likely limit of suspendability for the cobitolimod in the binary system.

TABLE 19

Results of API/Capryol PGMC limit of suspension study

| Approximate cobitolimod loading, mg/5 g Capryol | Observations AFTER spatula mix BUT BEFORE sonication | Observations AFTER spatula mix AND sonication |
|---|---|---|
| 200 mg (3.8% loading) | A thick paste was formed. | A fine, visibly uniform suspension was formed which was fluid and workable. |
| 400 mg (7.4% loading) | A thick paste was formed. | A fine, visibly uniform suspension was formed which was fluid and workable. |
| 600 mg (10.7% loading) | A thick paste was formed. | A fine, visibly uniform suspension was formed which was fluid and workable. |
| 800 mg (13.8% loading) | A thick paste was formed. | A fine, visibly uniform suspension was formed. Visibly, a slight increase in viscosity but the suspension was still fluid and workable. |
| 1000 mg (16.7% loading) | A thick paste was formed. | A fine, visibly uniform suspension was formed. Visibly, a large increase in viscosity, thick suspension at the limit of being workable/unworkable. |
| 1200 mg (19.4% loading) | A thick paste was formed. | The suspension very thick and unworkable. |

2.7 Preliminary Dispersion Testing of HPMC/Capryol Mix Results

Based on the limit of suspendability study, five mixes of HPMC in Capryol PGMC from 5% to 15% HPMC 1 (High molecular weight HPMC) (Table 15) and a blend of HPMC 1 (High molecular weight HPMC) and HPMC 2 (Low molecular weight HPMC; Table 16) were prepared for dispersion study. The results of the HPMC/Capryol only dispersion study are detailed in Table 20 below. The data confirms that the high molecular weight HPMC 1 mixes all form an effective gelling matrix. The higher the concentration of HPMC 1, the longer the dispersion time.

TABLE 20

Preliminary Dispersion testing of HPMC/Excipient mix results

| Mix | Initial time point | 2 minute time point | 5 minute time point | 30 minute time point | 1 hour time point |
|---|---|---|---|---|---|
| Mix 1 Placebo | Mostly aggregated together but not a solid gel. Same clear oily drops separate. | As for initial time point. | One big very fine gel drop. Clear oily drops still separate | Soft gel drop formed. Clear oily drops still separate | As for 30 minute time point |
| Mix 2 Placebo | Mostly aggregated together but not a solid gel. Same clear oily drops separate. | As for initial time point. | One big very fine gel drop. Clear oily drops still separate | Soft gel drop formed. Clear oily drops still separate | As for 30 minute time point |
| Mix 3 Placebo | Mostly aggregated together but not a solid gel. Same clear oily drops separate. | As for initial time point. | Several gel drops formed. Clear oily drops still separate. | Soft gel drop formed. Clear oily drops still separate | As for 30 minute time point |
| Mix 4 Placebo | No aggregation, separate small opaque drops formed but not a solid gel. | As for initial time point. | Several gel drops formed. Clear oily drops still separate. | As for 5 minute time point. | As for 30 minute time point |
| Mix 5 Placebo | No aggregation, separate small opaque drops formed but not a solid gel. | As for initial time point. | Several gel drops formed. Clear oily drops still separate. | Several solid gel drops formed. Clear oily drops still separate. | As for 30 minute time point |

| Mix | 2 hour time point | 3 hour time point | 4 hour time point | 5 hour time point | 24 hour (settling) time point |
|---|---|---|---|---|---|
| Mix 1 Placebo | Gel drop about 50% remaining. | Small gel fragments left, about 10% remaining. | As for 3 hour time point. | As for 4 hour time point. | Fully dissolved, no fragments visible. |
| Mix 2 Placebo | Gel drop about 50% remaining. | Small gel fragments left, about 20% remaining. | As for 3 hour time point. | As for 4 hour time point. | Fully dissolved, no fragments visible. |
| Mix 3 Placebo | Gel drop about 75% remaining and starting to fragment. | Gel drop has fragmented into several small pieces. Gel appears soft with about 60% remaining. | Gel fragments starting to break up. | As for 4 hour time point. | Fully dissolved, no fragments visible. |
| Mix 4 Placebo | Gel drops now just small fragments. | Appears to be fully in solution, no visible fragments left | As for 3 hour time point. Fully in solution | As for 4 hour time point. Fully in solution. | Fully dissolved, no fragments visible. |
| Mix 5 Placebo | Gel drops still formed but starting to disintegrate | Several drops remaining, reduced in size from 2 hour time point. | Small gel drops remaining, greatly reduced in size from 3 hour time point. Structure appears reasonably intact with same slight fraying at edges of drops. | As for 4 hour time point. | Fully dissolved, no fragments visible. |

2.8 Cobitolimod/Capryol/HPMC Formulation Study Results

Based on the suspension loading studies of the cobitolimod and HPMC in Capryol PGMC, and the assessment of the dispersion characteristics of the HPMC/Capryol mixtures in water, a number of prototype formulations were prepared as described in Section 2.4 in Tables 17 and 18.

While preparing these samples after the final addition of cobitolimod the mixes became thick unworkable pastes, this was probably due to the quantity of cobitolimod being too much when added at each step, causing overloading the system's ability to form a suspension. This is explained by the overall concentration of cobitolimod in the total formulation being 11.5% but the actual concentration of cobitolimod with respect to the Capryol PGMC excipient was between 12.1% and 13.5% which is nearing the limit of suspension. Extra Caproyl PGMC was added and the mixes sonicated at 25° C. until a uniform suspension was achieved. Extra quantities of HPMC and cobitolimod were added in smaller steps to bring the formulations up to the correct compositions, however after the final addition of the API all 5 mixes became thick pastes again. The mixes were then high shear mixed for periods of 1 minute ensuring the temperature remained below 30° C., after the final high shear mix all formulations were sonicated for 15 minutes at 25° C. with the results detailed in Table 21 below.

These results show that the maximum level of HPMC that can be accommodated in the tertiary mixes, at 11.5% cobitolimod loading, is about 10%.

TABLE 21

Formulation of cobitolimod/HPMC/Capryol mix results

| Mix | 1st high shear mixing cycle | 2nd high shear mixing cycle | 3rd high shear mixing cycle | 4th high shear mixing cycle | 5th high shear mixing cycle |
|---|---|---|---|---|---|
| 1 Active | Thick paste, possible slight visible reduction in viscosity. Still unworkable. | Visibly viscous suspension, visibly uniform throughout. Still unworkable. | Visible moderate viscous suspension, uniform throughout. Workable. | No change from 3rd mix. | Not performed as no change between and 3rd and 4th mix and suspension is workable. |
| 2 Active | Thick paste, slight visible reduction in viscosity. Still unworkable. | No change from 1st mix. | Thick uniform suspension, visible decrease in viscosity. Still unworkable. | No change from 3rd mix. | Possibly shear thinning, with effect lasting for 1 minute after mix stopped. Possibly workable. |
| 3 Active | Very thick paste. Unworkable. | No change from 1st mix. | No change. | No change. | Not performed as still thick unworkable paste |
| 4 Active | Thick paste, slight visible reduction is viscosity. Still unworkable | Thick visibly viscous suspension, visibly uniform throughout. Still unworkable. | Visibly moderate viscous suspension, unifrom throughout, workable. | No change from 3rd mix. | Not performed as no change between 3rd and 4th mix. Workable |
| 5 Active | Thick paste. Unworkable | No change from 1st mix. | No change. | No change. | Not performed as still thick unworkable paste. |

2.9 Cobitolimod/Excipient/HPMC Dispersion Testing Results

The dispersion study was performed using mixes 1 Active (5% HPMC1, HMW), 2 Active (10% HPMC 1, HMW) and 4 Active (5% HPMC1 and 5% HPMC2) as these were the only mixes which were workable. The results for the dispersion assessment of the API/Capryol/HPMC are detailed in Table 22.

A dispersion evaluation for a binary mixture of an active and Capryol was also carried out. The dispersion appeared to be immediate and fully dispersed upon adding the formulation to water.

TABLE 22

API/Excipient/HPMC dispersion testing results.

| Mix | Initial time point | 5 minute time point | 30 minute time point | 1 hour time point | 2 hour time point |
|---|---|---|---|---|---|
| Mix 1 Active | Small off white droplets formed. Several oily drops visible on water surface. No flocking of droplets. | As for initial time point. | Slight reduction in droplet size. Oil drops still visible. No flocking of droplets. | Droplets appear reduced in size and are less structurally defined. Off white colour fading and becoming slightly more transparent. No flocking of droplets. | Droplets greatly reduced in size. Number of droplets reduced. Oil drops still evident No flocking of remaining droplets. |
| Mix2 Active | Small off white droplets formed. Several oily drops visible on water surface. No flocking of droplets. | As for initial time point. | Slight reduction in droplet size. Oil drops still visible. No flocking of droplets. | Droplets appear reduced in size and are less structurally defined. Off white colour fading and becoming slightly more transparent. No flocking of droplets. | Droplets greatly reduced in size. Oil drops still evident. No flocking of remaining droplets. |
| Mix4 Active | Small off white droplets formed. Several oily drops visible on water surface. No flocking of droplet s. | As for initial time point. | Slight reduction in droplet size. Oil drops still visible. No flocking of droplets. | Droplets appear reduced in size. Still structurally similar to 30 minute time point. Off white colour fading and becoming slightly more transparent. No flocking of droplets. | Droplets greatly reduced in size. Water is slightly cloudy. Oil drops still evident. No flocking of remaining droplets. |
| Mix | 3 hour time point | 4 hour time point | 5 hour time point | 24 hour (settling) time point |
|---|---|---|---|---|
| Mix 1 Active | Very small fragments remaining, mast droplets have solubilised. Oil drops still evident. | Appears fully solubilised. Oil drops still evident. | As per 4 hour time point. Appears fully solubilised. | Appears fully solubilised. |
| Mix2 Active | Small fragments remaining, most droplets have solubilised. Oil drops still evident. | As for 3 hour time point. | As per 4 hour time point. | Appears fully solubilised. |
| Mix4 Active | Appear s fully solubilised Oil drops still evident. | As for 3 hour time point. Appears fully solubilised. | As per 4 hour time point. Appears fully solubilised. | Appears fully solubilised. |

It appears that all formulations form a gelling matrix on contact with water. These matrices would erode over time. The 3 hrs assessment data (Table 22) suggests that the presence of the low molecular weight HPMC would accelerate the erosion process. The data also suggests that the dispersion of the formulation comprising cobitolimod appears to be faster than the binary mixes of the HPMC in Capryol PGMC, which suggests that the hydrophilic nature of the cobitolimod may have facilitated dosage form dispersion.

2.10 Conclusions

This study has shown that there is a limit of cobitolimod incorporation with the Capryol PGMC binary system of about 13%. A gel system based on HPMC that can potentially modulate drug release can be prepared with 5-15% HPMC. Based on this understanding, five Prototype formulations incorporating 11.5% cobitolimod, 5-15% HPMC were evaluated. 11.5% w/w cobitolimod loading with respect to the complete formulation was chosen as this gives an cobitolimod loading with respect to the Capryol PGMC of between 13.7% and 15.6% (the HPMC is assumed not to contribute to improving the cobitolimod loading but is incorporated as a release modifier). Based on the assessment of the dispersion characteristics of these formulations, it is recommended that between 5%-10% high molecular weight HPMC 1 can be used as the base formulation for a study evaluating coating to target colon release.

Example 3—Preparation of Core Formulations Containing Antioxidants and Buffering Agents The excipients and other materials used in this Example are detailed in Table 23 below.

TABLE 23

| Materials | |
|---|---|
| Material | Manufacturer |
| Capryol PGMC | Gattefosse |
| Methocel K100M (HPMC) | Dow |
| Tromethamine (pH buffer) | Sigma |
| BHT (Antioxidant) | Merck |
| X Bridge BEH C18 column | Waters |
| Acetonitrile | VWR |
| TEA | Fisher |
| HFIP | Aldrich |
| Water | In house |

3.1 Preparation of Capryol PGMC and Cobitolimod Base Formulation

The composition of the Capryol PGMC and cobitolimod base formulation is detailed in Table 24. The Capryol PGMC and cobitolimod base formulation was prepared as follows, 13.37 g of Capryol PGMC was weighed into a vessel. To this, 1.84 g of cobitolimod API was added in multiple steps of between 0.4 g and 0.5 g. Between each addition of API, the formulation was mixed by spatula, before high shear mixing for periods not exceeding 1 minute and 30° C., until a fluid and visibly uniform suspension was achieved. To this suspension, 0.8 g of Methocel K100M HPMC was added and mixed by spatula, before again high shear mixing for periods not exceeding 1 minute and 30° C., until a fluid and visibly uniform suspension was achieved. Two samples of approximately 2 g of the suspension were removed. One sample was stored at 2-8° C., prior to analysis, then second sample was set down on stability at 40°/75% RH.

TABLE 24

| Material | Composition (% w/w) |
|---|---|
| Cobitolimod | 11.5 |
| Methocel K100M | 5.0 |
| Capryol PGMC | 83.5 |

3.2 Preparation of Capryol PGMC, Cobitolimod and Antioxidant Formulation

The composition of the Capryol PGMC, cobitolimod and antioxidant formulation is detailed in Table 25. From the formulation prepared in section 3.1, Capryol PGMC and cobitolimod base formulation, 12 g of the sample was weighed to a vessel and to this, 0.012 g of BHT was added. The formulation was then high shear mixed for periods not exceeding 1 minute or 30° C., until a fluid and visibly uniform suspension was achieved. Two samples of approximately 2 g of the suspension were removed. One sample was stored at 2-8° C., prior to analysis, then second sample was set down on stability at 40°/75% RH.

TABLE 25

| Capryol PGMC, cobitolimod and antioxidant formulation composition | |
|---|---|
| Material | Composition (% w/w) |
| Cobitolimod | 11.5 |
| Methocel K100M | 5.0 |
| Capryol PGMC | 83.5 |
| BHT | 0.1* |

*Quantity of is deemed to have a negligible impact on the overall composition of the formulation therefore no recalculation of the composition is required 3.3 Preparation of Capryol PGMC, Cobitolimod, Antioxidant and pH Buffer Formulation The composition of the Capryol PGMC, cobitolimod, antioxidant and pH buffer formulation is detailed in Table 26. From the sample prepared in section 3.2, Capryol PGMC, cobitolimod and antioxidant formulation, 6 g of sample was weighed to a vessel and to this 0.03 g of Tromethamine was added. The formulation was then high shear mixed for periods not exceeding 1 minute or 30° C., until a fluid and visibly uniform suspension was achieved. Two samples of approximately 2 g of the suspension were removed. One sample was stored at 2-8° C., prior to analysis, then second sample was set down on stability at 40°/75% RH.

TABLE 26

| Capryol PGMC, cobitolimod, antioxidant and pH buffer formulation composition | |
|---|---|
| Material | Composition (% w/w) |
| Cobitolimod | 11.5 |
| Methocel K100M | 5.0 |
| Capryol PGMC | 83.5 |
| BHT | 0.1* |
| Tromethamine | 0.5* |

*Quantity of is deemed to have a negligible impact on the overall composition of the formulation therefore no recalculation of the composition is required 3.4 Physical and Chemical Stability Assessments The bulk mixes were assessed physically and chemically initially and following four weeks of storage at 40° C./75% RH. For the physical assessments, samples were assessed visually for appearance changes, focusing on colour and physical behaviour.

For the chemical analysis the following method was used:

The samples were run on an X Bridge BEH C18, 2.5 µm, 4.6 mm×50 mm column with a flow rate of 0.4 ml/min at 60° C., a run time of 60 minutes and a detection wavelength of 260 nm. The sample injection volume was 40 with a sampler temperature of 5° C. The mobile phase compositions were as follows:

Mobile phase A 3% Acetonitrile in 0.2% TEA, 1% HFIP,
Mobile phase B 12% Acetonitrile in 0.2% TEA, 1% HFIP,
Mobile phase C Acetonitrile,
Mobile phase D water.

The sample identifiers for stability set down were as follows.

1233/071/01 T=0 week time point Capryol PGMC and cobitolimod base formulation as section 3.1
1233/071/02 T=4 week time point Capryol PGMC and cobitolimod base formulation as section 3.1
1233/072/01 T=0 week time point Capryol PGMC, cobitolimod and antioxidant formulation as section 3.2
1233/072/02 T=4 week time point Capryol PGMC, cobitolimod and antioxidant formulation as section 3.2
1233/072/03 T=0 week time point Capryol PGMC, cobitolimod, antioxidant and pH buffer formulation as section 3.3
1233/072/04 T=4 week time point Capryol PGMC, cobitolimod, antioxidant and pH buffer formulation as section 3.3

3.5 Physical Assessments

The formulations were physically assessed prior to and following four weeks of stability storage at 40° C./75% RH. All three formulations formed white suspensions and no physical changes were evident following stability storage.

3.6 Chemical Assessments

The formulations were chemically assessed for assay and related substances, prior to and following four weeks of stability storage at 40° C./75% RH. The average results are summarised in Table 27 with the individual results in Table 28. The assay results show some variability between the initial and the four week time point (increase of 13.8% for the base, decrease of 9.1% for the base with antioxidant and increase of 8.9% for the base with antioxidant and pH buffer), however this is common at this stage, due to homogenisation of small volume samples and the method is not formulation specific. For this reason, related substance levels are used as an indicator of stability. The results show that for all three formulations, the change in related substances is very low over a 4 week period. For the base formulation, related substances increased by 0.67%, for the base formulation with antioxidant, the related substances decreased by 0.67% and for the base formulation with antioxidant and pH buffer, the related substances decreased by 0.07%. Both formulations with additional excipients demonstrated an improvement in chemical stability over the base formulation, following four weeks of storage at 40° C./75% RH.

The base formulation results compared favourably with previous results from Example 1. The related substances in the previous study were shown to be 5.24% (for T=0) and 7.05% (for T=4), compared to 5.31% (T=0) and 6.07% (T=4) in this study, showing that the base formulation does suffer from slight degradation. Based on the results observed, it is suggested that an antioxidant is included in the formulation. In addition, to support increased handling during manufacture, it is suggested that tromethamine pH buffer is also included.

Furthermore, the impurity level of the reference cobitolimod raw material (5.3 area %) is similar to the T=0 result which indicates the material was stable during the formulation process.

It is also noted that during the manufacture, the tromethamine pH buffer showed some insolubility in the Capryol PGMC, with the remaining insoluble tromethamine forming a very fine suspension. Therefore the tromethamine may be suspended in the prototype formulation moving forward.

TABLE 27

Results of T = 0 and T = 4 week time points

| Formulation | Assay (% w/w) * | | | Related substances (relative area %) * | | |
|---|---|---|---|---|---|---|
| | T = 0 week | T = 4 week | Difference (%) T = 0 and T = 4 | T = 0 week | T = 4 week | Difference (%) T = 0 and T = 4 |
| Base | 113.3 | 127.1 | +13.8% | 5.31 | 5.98 | +0.67% |
| Base, antioxidant | 111.3 | 102.2 | −9.1% | 6.33 | 5.66 | −0.67% |
| Base, antioxidant, pH buffer | 108.5 | 117.3 | +8.9% | 5.40 | 5.33 | −0.07% |

* Results are average of duplicate analysis.

TABLE 28

Individual results of T = 0 and T = 4 week time points.

| Formulation | | Assay (% w/w) | | Related substances (relative area %) | |
|---|---|---|---|---|---|
| | | T = 0 week | T = 4 week | T = 0 week | T = 4 week |
| Base | Sample 1 | 113.8 | 125.7 | 5.40 | 5.92 |
| | Sample 2 | 112.8 | 128.4 | 5.22 | 6.04 |
| Base, antioxidant | Sample 1 | 111.9 | 87.1 | 5.90 | 5.65 |
| | Sample 2 | 110.6 | 117.3 | 6.75 | 5.66 |
| Base, antioxidant, pH buffer | Sample 1 | 108.6 | 118.7 | 5.11 | 5.34 |
| | Sample 2 | 108.3 | 115.9 | 5.68 | 5.32 |

3.7 Conclusion

The results show that for all three formulations, the change in related substances is very low over a 4-week period at elevated temperature. For the base formulation, the highest increase in impurities was reported. Both formulations with additional excipients demonstrated unchanged or decreased level of impurities, following four weeks of storage at 40° C./75% RH. Based on the results observed, the incorporation of an antioxidant with/without pH buffer is compatible with Capryol PGMC/cobitolimod and has a positive stabilizing effect on chemical degradation. In addition, the formulation process did not cause any chemical degradation of the mixture.

Example 4—Coating

The excipients, API and other materials used in this study are detailed in Table 29 below and are as per the previous Examples.

TABLE 29

| Materials used |
| --- |
| Material |
| Cobitolimod |
| Methocel K100M |
| Capryol PGMC |
| BHT |
| Tromethamine |
| Coni-Snap size 1 white opaque gelatin |
| Gelatin 220 bloom |
| Sterile water for irrigation |
| Eudragit L30 D-55 |
| Eudragit FS 30 D |
| Triethyl Citrate |
| Talc |
| Bulking capsules for coating |

4.1 Preparation of Bulk Mix for Uncoated Capsules and Capsule Preparation

The bulk mix was first prepared in a stainless steel vessel. The formulation composition and required weights for 140 capsules is detailed in Table 30. The required quantity of Capryol PGMC (41.604 g) was dispensed into a suitable vessel and to this, 0.050 g of BHT and 0.200 g of tromethamine was added. The formulation was then high shear mixed for periods not exceeding 5 minutes and 30° C., until all solid materials were fully dissolved. The required quantity of cobitolimod (6.663 g) was then dispensed in aliquots to the mix and mixed by spatula to wet the powder. The formulation was then high shear mixed for periods not exceeding 5 minutes and 30° C., until a homogeneous suspension was achieved. Following on from this mixing, to the homogeneous suspension, the required quantity Methocel K100M (of 2.281 g) was added and mixed by spatula to wet the powder. The formulation was then again high shear mixed for periods not exceeding 5 minutes and 30° C., until a homogenous suspension was achieved.

Following preparation, the mix was then hand filled into size 1 white gelatin Coni-Snap capsules, to a target fill weight of 362.6 mg with upper limit 389.8 mg and a lower limit 335.4 mg. The filled capsules were then banded using a standard 25% gelatin banding solution, on the Quali-Seal bench scale banding machine. The banded capsules were then left to air dry for a minimum of 6 hours at room temperature. Following this, the capsules were subjected to vacuum testing (<−20 mmHg) and then visually checked for any signs of leaking capsules. Finally, the capsules were stored in double polythene bags in the fridge at 2-8° C. until required for coating.

TABLE 30

| | Formulation composition. | | | |
| --- | --- | --- | --- | --- |
| RAW MATERIAL | Unit Formulation (%) w/w | Nominal Unit Formulation (mg) | Corrected Unit Formulation (mg) | CORRECTED BATCH QUANTITY* (g) |
| Cobitolimod | 11.5 | 41.70 | 47.54 | 6.66 |
| Methocel K100M | 4.5 | 16.32 | 16.32 | 2.28 |
| Capryol PGMC | 83.5 | 302.77 | 296.93 | 41.57 |
| BHT | 0.1 | 0.36 | 0.36 | 0.05 |
| Tromethamine | 0.4 | 1.45 | 1.45 | 0.20 |
| Total | 100.00 | 362.60 | 362.60 | 50.76 |

*The corrected batch quantity of cobitolimod is calculated as: [(target batch size) × (41.7 × 1.14] (calculations are rounded at the second decimal place)

The correction factor for the assay of cobitolimod is 1.14. The corrected quantity of Capryol PGMC is calculated as: total batch quantity−[(corrected batch quantity of cobitolimod)+(batch quantity of Methocel K100M)+(batch quantity of BHT)+(batch quantity of Tromethamine)].

4.2 Preparation of Coating Solution 1 and Coating Solution 2

The following details the preparation method followed for both coating solutions. Table 31 details the composition and weights required for coating solution 1 and Table 32 details the composition and weights required for coating solution 2. The required quantities of Eudragit L30 and Eudragit FS30 were dispensed into a suitable vessel and stirred for a minimum of 10 minutes, using a magnetic stirring plate. Following mixing, the required quantity of sterile water (254.15 g) was dispensed into a separate vessel. To this, the required quantity of talc was dispensed and mixed by spatula to wet the talc (27.50 g). The required quantity of Triethyl Citrate was then dispensed into the vessel containing the water and talc and the mix was high shear mixed for a minimum of 10 minutes, until a homogeneous suspension was formed. The water/talc/Triethyl Citrate mix was added slowly to the Eudragit L30 and FS30 mix and the suspension was stirred for a minimum of 10 minutes, before being filtered through a stainless steel sieve of ≤500 μm. The filtered mix was kept stirring until required for coating.

TABLE 31

| Composition and weights required for coating solution 1 | | |
| --- | --- | --- |
| RAW MATERIAL | Unit formulation (% w/w) | BATCH QUANTITY (g) |
| Eudragit L30 D-55 (per unit mix) | 20.835 | 104.175 |
| Eudragit FS 30 D (per unit mix) | 20.835 | 104.175 |
| Talc (per unit mix) | 5.50 | 27.50 |
| Triethyl Citrate (per unit mix) | 2.00 | 10.00 |
| Sterile Water for Irrigation | 50.83 | 254.15 |
| Total | 100.00 | 500.00 |

TABLE 32

Composition and weights required for coating solution 2

| RAW MATERIAL | Unit formulation (% w/w) | BATCH QUANTITY* (g) |
|---|---|---|
| Eudragit ® L30 D-55-(per unit mix) | 10.42 | 52.10 |
| Eudragit ® FS 30 D-(per unit mix) | 31.25 | 156.25 |
| Talc (per unit mix) | 5.50 | 27.50 |
| Triethyl Citrate-(per unit mix) | 2.00 | 10.00 |
| Sterile Water for Irrigation | 50.83 | 254.15 |
| Total | 100.00 | 500.00 |

4.3 Capsule Coating

Capsules were coated with either coating solution 1 or coating solution 2. In total 43 capsules were coated per coating solution. The required number of capsules to be coated were added to the coating machine bowl. The capsules were coated using a fluid bed coating machine (the Strea-1). The capsules were weight checked periodically throughout the coating process and adjustments to the coating application rate were made if required. Coating continued until the capsules had been coated to a target of 50 mg per capsule. The capsules were then allowed to cure at room temperature, before being visually sorted to remove any defective capsules. Finally, the capsules were stored in a fridge at 2-8° C., prior to dissolution testing.

4.4 Dissolution Testing

The dissolution testing was carried out at 37° C. in a two buffer stage process (0.1M HCl initially for two hours, using a visual check for capsule rupture, before transferring the capsules to a pH 6.8 phosphate buffer stage until completion). USP apparatus 2 was used with a paddle speed of 50 rpm, media volume of 900 ml and a sample volume of 1 ml. Samples were taken during the pH 6.8 buffer phase, at 5, 10, 15, 20, 30, 45, 60, 90, 120 mins, then 3, 4, 5, 6, 7, 8, 12, 18, 24 hour time points. Two capsules were tested for each capsule batch and time point (n=2). The samples were then analysed with one injection per capsule per time point.

For the chemical analysis the following method was used.

The samples were run on an X Bridge BEH C18, 2.5 µm column with a flow rate of 0.4 ml/min at 60° C., a run time of 16 minutes, a detection wavelength of 260 nm and a sampler temperature of 5° C. The mobile phase compositions were as follows:

Mobile phase A 3% Acetonitrile in 0.2% TEA, 1% HFIP,
Mobile phase B 12% Acetonitrile in 0.2% TEA, 1% HFIP.

4.5 Assessment of Formulation pH Buffer Level

In order to assess the tromethamine solubility and influence of this buffer on pH, 10 g mixes were prepared at the following Tromethamine loading 0.01%, 0.05%, 0.1%, 0.2%, 0.3%, 0.4% and 0.5% in Capryol PGMC in a scintillation vials. The vials were then high shear mixed for a minimum of 2×2 minutes then allowed to settle, all had visible insoluble material, therefore the samples were then high shear mixed for a further 2 minutes and visually assessed before samples taken for pH analysis. pH analysis involved centrifuging the sample at 14000 RPM for 10 minutes to separate out the insoluble material and then diluting 1 g of the clear supernatant with 3 g of deionised water, mixing thoroughly and measuring the pH.

Results and Discussion 4.6 Capsule Manufacture

The formulation was prepared without issue and the visual assessment of homogeneity was acceptable. The formulations were encapsulated by hand filling and banded using the Qualiseal bench scale bander, without any notable observations or problems. All capsules were filled within the acceptable weight range, with a minimum fill weight of 355.3 mg and a maximum fill weight of 383.0 mg. Upon vacuum sorting no capsules were found to be leaking, therefore all capsules were deemed acceptable. In order to fluidise the bulking capsules and the active capsules, a fan speed ranging from 4.75 to 7.25 was used. The capsules were evenly coated and the surface of the coat was smooth.

4.7 Results of the Uncoated and Coated Capsule Dissolution Testing

Figure 3:
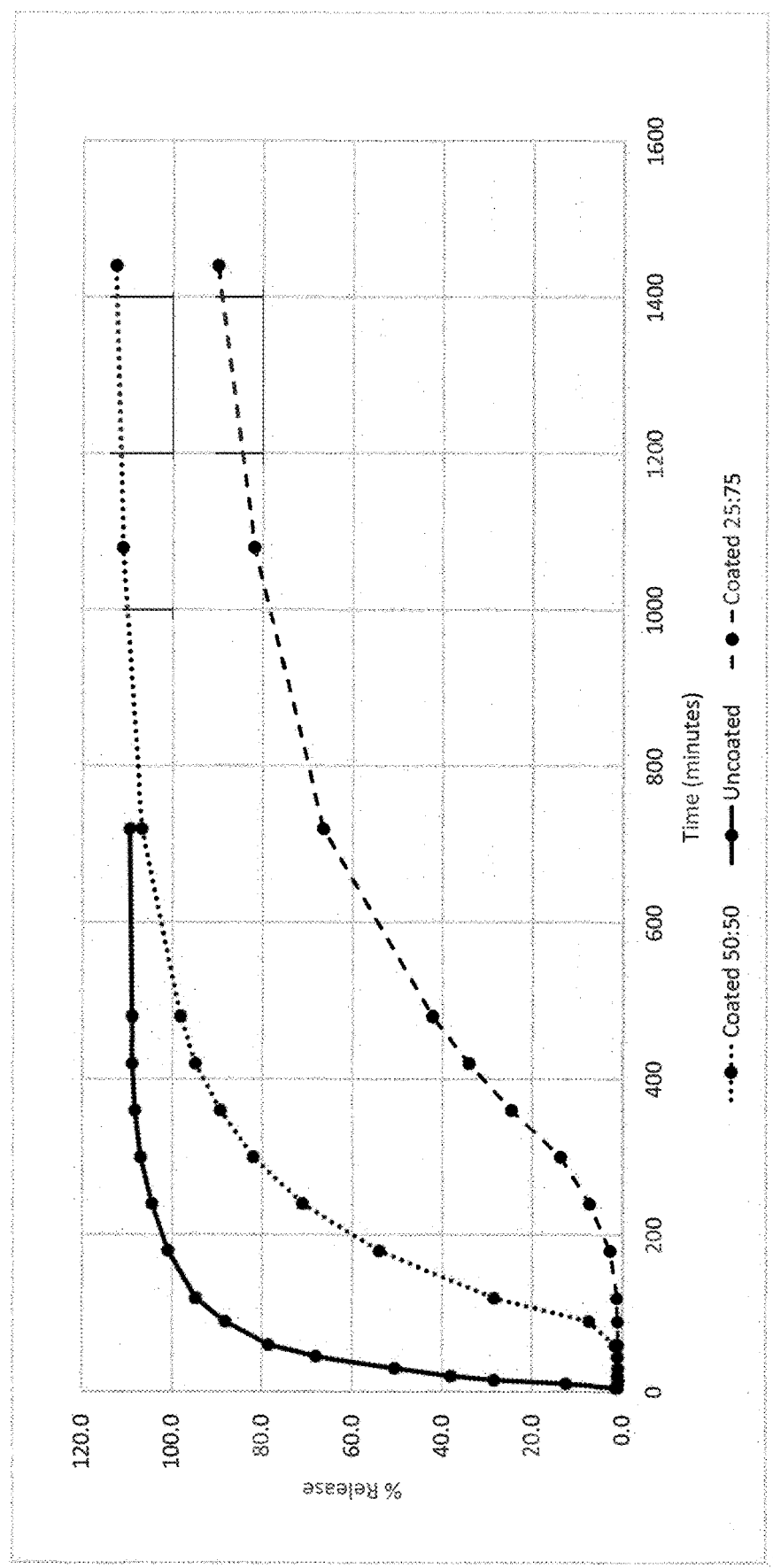
FIG. 3 shows the dissolution testing of uncoated and coated capsules.

Table 33 and FIG. 3 detail the results of the dissolution testing of the uncoated and coated capsules. The uncoated capsules were not exposed the two stage buffer dissolution assessment and were tested in pH 6.8 buffer only. The results showed that the uncoated capsules started to release cobitolimod within 5 to 10 minutes of exposure to pH 6.8 buffer, with 80% of cobitolimod release occurring within approximately 1½ hours. The capsules then achieved full release within approximately 3 hours. The results indicated that the HPMC gelling matrix, had an effect on slowing the release rate of cobitolimod from the capsule, potentially through the creation of a physical barrier. The barrier created by the formulation delayed the migration of cobitolimod from the formulation matrix to the dissolution media.

The capsules coated with coating solution 1 (50:50 L:S polymer ratio) showed no visual signs of capsule rupture during 2 hour exposure to 0.1 M HCl. Following transfer to pH 6.8 buffer, the capsules showed a delay in start of cobitolimod release, with release initiating after approximately 1 hour. The delay in release was due to the combination of Eudragit polymers used, with dissolution of the L30 polymer occurring on exposure to pH 6.8 media. The S polymer will offer greater resistance to the media than the L30 polymer and as the L30 polymer dissolves, the capsule shell will become exposed in parts, enabling cobitolimod to move into the dissolution media. The cobitolimod is then released steadily over approximately 10 hours, due to the combined effects of the pore size generated by the L30 polymer reducing the influx and efflux of the dissolution media and HPMC gel matrix limiting the amount of formulation that is released from the capsule core. Approximately 80% of the cobitolimod is released after 6 hours, after which the release rate slows until full release is achieved after approximately 12 hours.

The capsules coated with coating solution 2 (25:75 L:S polymer ratio) showed no visual signs of capsule rupture during 2 hour exposure to 0.1 M HCl. Following transfer to pH 6.8 buffer, the capsules showed a delay in start of cobitolimod release, with release initiating after approximately 2 hours. The delay in release was due to the combination of Eudragit polymers used, with dissolution of the L30 polymer occurring on exposure to pH 6.8 media. In comparison to the 50:50 coating polymer preparation, higher S polymer content will offer even greater resistance to the media and therefore the greater delay in release. The cobitolimod is then released steadily over approximately 16 hours, due to the combined effects of the pore size generated by the L30 polymer reducing the influx and efflux of the dissolution media and HPMC gel matrix limiting the amount of formulation that is released from the capsule core.

TABLE 33

Results of the dissolution testing of the uncoated and coated capsules.

| Time point (min) | Average % release from uncoated capsule | Average % release from 50:50 Eudragit L30 D-55:FS 30 D coated capsule (n = 6) | % RSD 50:50 Eudragit L30 D-55:FS 30 D coated capsule | Average % release from 25:75 Eudragit L30 D-55:FS 30 D coated capsule (n = 6) | % RSD 25:75 Eudragit L30 D-55:FS 30 D coated capsule |
|---|---|---|---|---|---|
| 5 | 1.5 | 0 | N/A | 0 | N/A |
| 10 | 12.5 | 0 | N/A | 0 | N/A |
| 15 | 28.5 | 0 | N/A | 0 | N/A |
| 20 | 38.1 | 0 | N/A | 0 | N/A |
| 30 | 50.6 | 0 | N/A | 0 | N/A |
| 45 | 68.1 | 0 | N/A | 0 | N/A |
| 60 | 78.5 | 1.5 | 59.0 | 0 | N/A |
| 90 | 88.1 | 5.5 | 46.5 | 0 | N/A |
| 120 | 94.7 | 15.9 | 65.9 | 0 | N/A |
| 180 | 100.9 | 38.8 | 51.6 | 5.2 | 142.5 |
| 240 | 104.5 | 53.4 | 33.7 | 11.1 | 113.0 |
| 300 | 107.1 | 67.7 | 22.1 | 20.1 | 93.4 |
| 360 | 108.3 | 77.3 | 17.0 | 29.8 | 64.3 |
| 420 | 108.9 | 86.6 | 10.3 | 43.2 | 36.0 |
| 480 | 109.0 | 90.6 | 8.5 | 52.1 | 23.1 |
| 720 | 109.5 | 100.3 | 7.2 | 70.3 | 12.3 |
| 1080 | N/A | 107.3 | 2.2 | 84.1 | 6.8 |
| 1440 | N/A | 109.8 | 1.2 | 94.9 | 8.8 |

RSD = relative standard deviation 4.8 Assessment of Formulation pH Buffer Level

The results of the study are detailed in Table 34. All of the samples showed some insolubility of the Tromethamine, with the lower loading samples 0.05% and 0.01% showing the least insolubility with just some fine insoluble material left. All the samples pH remained steady throughout, although the pH was possibly starting to lower at the 0.01% loading level.

TABLE 34

Tromethamine solubility and pH assessment results

| Mix | Dilution | pH | Comments |
|---|---|---|---|
| 0.5% Tromethamine in Capryol PGMC | 1 g Sample in 3 g water (4 g total) | 7.59 | Coarse insoluble material evident |
| 0.4% Tromethamine in Capryol PGMC | 1 g Sample in 3 g water (4 g total) | 7.69 | Coarse insoluble material evident |
| 0.3% Tromethamine in Capryol PGMC | 1 g Sample in 3 g water (4 g total) | 7.74 | Insoluble material evident |
| 0.2% Tromethamine in Capryol PGMC | 1 g Sample in 3 g water (4 g total) | 7.63 | Insoluble material evident |
| 0.1% Tromethamine in Capryol PGMC | 1 g Sample in 3 g water (4 g total) | 7.61 | Insoluble material evident |
| 0.05% Tromethamine in Capryol PGMC | 1 g Sample in 3 g water (4 g total) | 7.68 | Very fine insoluble material evident (high shear mixed for 4 × 2 minute periods) |
| 0.01% Tromethamine in Capryol PGMC | 1 g Sample in 3 g water (4 g total) | 7.42 | Very fine insoluble material still evident after first round of high shear mixing (3 × 2 minutes). Sample then heated to 60° C. for 30 minutes then high shear mixed again (1 × 2 minutes), insoluble material still evident. |
| 1 g Capryol PGMC in 3 g water | 1 g Sample in 3 g water (4 g total) | 6.99 | N/A |

4.9 Conclusion

Capsules containing cobitolimod and excipients were successfully manufactured. The capsules were then coated with a combination of Eudragit L30 D-55 and FS 30D, at a ratio of 50:50 or 25:75. Both coated and uncoated capsules were subjected to dissolution testing. The uncoated capsules were subjected to pH 6.8 buffer only and demonstrated sustained release over 3 hours. The coated capsules were subject to 2 hours in 0.1 M HCl, followed by pH 6.8 phosphate buffer for 24 hours. Both coatings prevented capsule rupture within acidic media, followed by a sustained release in pH 6.8 phosphate buffer, enabled by the coating polymers, combined with the HPMC gelling matrix. Based on the results obtained, the release profile can be altered by varying the ratio of L to S coating polymer, whilst maintain the capsule fill formulation.

Example 5—Bulk Testing Data

As part of the technical batch manufacture, bulk mix uniformity and capsule content uniformity was assessed over the filling period.

5.1 Materials

Details of all materials used throughout this study are outlined in Table 35.

TABLE 35

Materials used for the technical batch manufacture

| Material | Manufacturer |
|---|---|
| Cobitolimod | Avecia |
| Methocel K100M | Colorcon |
| Capryol PGMC | Gattefosse |
| BHT | Merck |
| Tromethamine | Sigma |
| Coni-Snap size 1 white gleatin capsules | Capsugel |
| Gelatin 220 Bloom | Gelita |
| Sterile water for irrigation | Fresnius Kabi |

TABLE 35-continued

Materials used for the technical batch manufacture

| Material | Manufacturer |
|---|---|
| Eudragit L30 D-55 | Evonik |
| Eudragit FS 30D | Evonik |
| Triethyl citrate | Merck |
| Talc | Merck |
| Aclar film for blister packing (Techniflex Europe | Tekni-Plex |
| White indexed unprinted aluminium | Amcor Flexibles |

5.2 Bulk Mix Preparation

Details of the formulation composition are provided in Table 36. The formulation was prepared in a labelled stainless steel vessel with lid and 114.0 g of Capryol PGMC was added. To the Capryol PGMC, 0.139 g of BHT was added and the resultant mixture high shear mixed at full speed for 2 minutes, under nitrogen, until the BHT was fully dissolved. Following this, to the mix 0.278 g of Tromethamine was added and homogenised under nitrogen, using the high shear mixer at full speed for 2 periods of 5 minutes, until the Tromethamine was visually fully homogenised. A total of 18.26 g of cobitolimod was added to the bulk mix in aliquots and high shear mixed under nitrogen at full speed for 4×5 minute and 1×2 minute periods, until a visibly homogeneous suspension was achieved. Finally, 6.24 g of Methocel K100M was added in aliquots and high shear mixed at full speed under nitrogen for 1×5 and 1×4 minute periods, until a visibly homogeneous suspension was achieved. The mix was then degassed for 8 minutes at a vacuum of −21 in Hg (inches. Mercury) to remove air present in the bulk mix and ensure effective filling on a Hibar filling machine.

TABLE 36

Formulation for the 41.7 mg cobitolimod bulk mix

| RAW MATERIAL | Unit Formulation (%) w/w | Nominal Unit Formulation (mg) | Correct for API purity unit formulation (mg) | Nominal corrected batch |
|---|---|---|---|---|
| Cobitolimod | 11.5 | 41.70 | 47.54 | 18.21 |
| Methocel K100M | 4.5 | 16.32 | 16.32 | 6.25 |
| Capryol PGMC | 83.7 | 303.50 | 297.65 | 114.0 |
| BHT | 0.1 | 0.363 | 0.363 | 0.139 |
| Tromethamine | 0.2 | 0.725 | 0.725 | 0.278 |
| Total | 100.00 | 362.60 | 362.60 | 138.89 |

5.3 Capsule Filling and Banding, Bulk Mix Sampling and pH Assessment Method

The HiBar filling machine was set up with size 1 tooling. The empty weight of 12 capsules was calculated and used to calculate the limits on the filling weight control chart. The bulk mix was then transferred to the HiBar hopper, maintained under nitrogen and stirred using an overhead stirrer set to 112 rpm. The HiBar was then set to fill at the target weight of 362.6 mg, with limits of 389.8 mg (upper) and 335.4 mg (lower). Filling commenced with capsule weights being monitored throughout the run at 15 minute intervals.

The pH of the formulation was assessed by sampling 0.5 g of bulk mix from the start, middle and end of the manufacturing run and diluting the sample with 5 g of deionised water (4 g of deionised water was initially used but a further 1 g of deionised water was added for processability). The pH was then measured using a handheld pH probe.

The capsules were then banded with a 25% gelatin banding solution on the Quailseal bench scale bander using size 1 tooling. Following completion of the filling and banding stage the capsules were left to dry at ambient temperature. During capsule banding ten capsules for each time point were separated for content uniformity assessment from the start, middle and end of the manufacturing run.

5.4 Coating Suspension Preparation

The coating suspension was prepared using the following method, 156.28 g of Eudragit L30 D-55 and 156.30 g of Eudragit FS 30D were weighed into a vessel and stirred using a magnetic stirrer for at least 10 minutes (Table 37). To a second vessel 381.27 g of sterile water was weighed and to this 41.26 g of talc was added, this was then mixed by spatula to wet the talc. When the talc was fully wetted, 15.01 g of Triethyl Citrate was added and the mix stirred by spatula. This mix was then high shear mixed at full speed for at least 10 minutes to create a visually homogeneous suspension. The resulting suspension was then added to the Eudragit mixture and was stirred using a magnetic stirrer for at least 10 minutes, before being filtered through a 500 μm stainless steel sieve. The filtered suspension was maintained under constant stirring.

TABLE 37

Nominal composition of the coating suspension

| RAW MATERIAL | Unit formulation (% w/w) | Nominal bulk formulation (g) |
|---|---|---|
| Eudragit ® L30 D-55-(per unit mix) | 20.835 | 156.26 |
| Eudragit ® FS 30 D-(per unit mix) | 20.835 | 156.26 |
| Talc (per unit mix) | 5.500 | 41.25 |
| Triethyl Citrate-(per unit mix) | 2.000 | 15.00 |
| Sterile Water for Irrigation | 50.830 | 381.23 |
| Total | 100.00 | 750.00 |

5.5 Capsule Coating Method

The filled and banded capsules were counted to give an exact number of capsule to be coated and the target coated capsule weight was calculated using the filled and banded average capsule weight. The coating machine was set up and the setting of the peristaltic pump was adjusted to give the required flow rate of coating suspension. The capsules were then transferred to the coating machine, fluidised and coating was commenced. The coating was seen to be even and smooth on the capsules. The capsules were then allowed to cure at ambient temperature. The capsules were then visually inspected and any defective capsules removed. The average weight of the remaining coated capsules was determined and the capsules were then stored in double polythene bags at 2-8° C.

5.6 Blister Packing Method.

The bench blister packing machine was set up and 10 empty blister strips were prepared for leak testing, to confirm machine performance. The 10 empty blister strips were then submerged in water and subjected to a vacuum of 0.5 bar absolute for 30 seconds and then visually assessed for any failed pockets. The capsules were then blister packed until completion, after which a further 10 empty blisters were prepared and the leak test was repeated. The full blisters were then labelled before being stored at 2-8° C. prior to stability set down.

Results and Discussion 5.7 Technical Batch Manufacture

Figure 5:
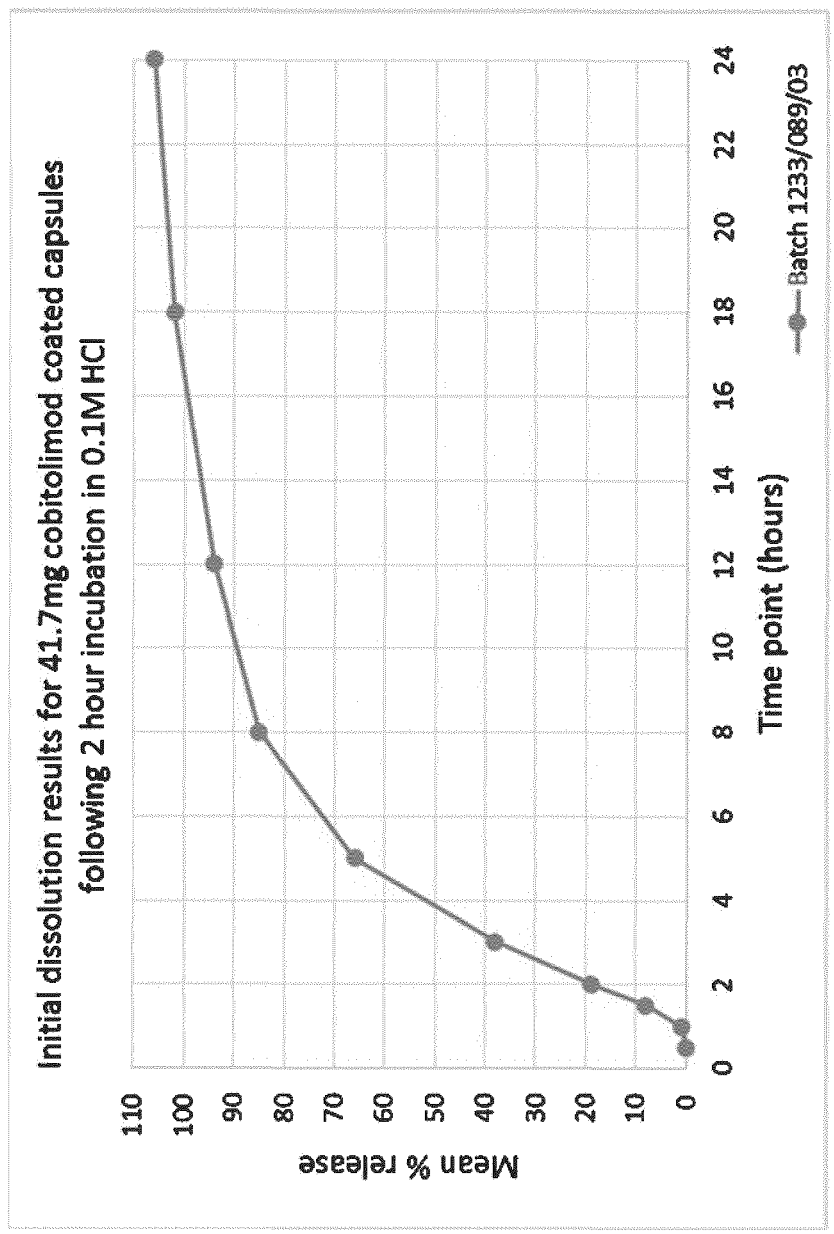
FIG. 5 shows the results of initial dissolution of coated capsules cobitolimod prepared in Example 5.

In total 306 capsules were available following filling and banding, from these capsules 30 capsules were sampled for content uniformity testing. From the visual sort 9 capsules were removed due to bubbles in the band or incomplete banding. The coating of the capsules was carried out with no issues occurring during the coating process. In total 267 were coated. Finally, as capsules were blister packed in blisters containing ten capsules, 260 capsules were blisters packed, the remaining 7 capsules were blister packed and the empty blister pockets cut off. The results from the initial dissolution testing are shown in FIG. 5.

5.8 Bulk Mix and Content Uniformity Assessment

Figure 4:
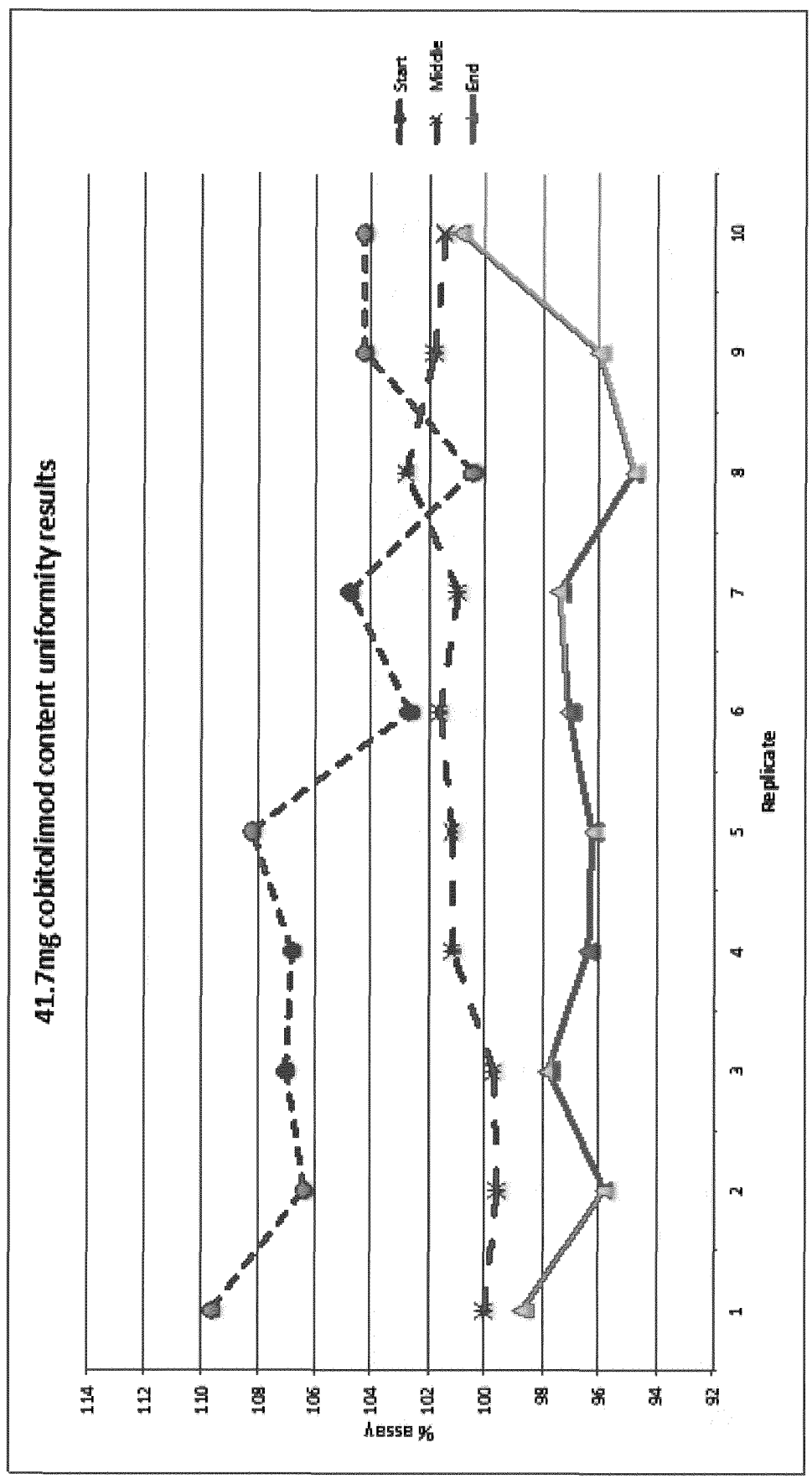
FIG. 4 shows the content uniformity results at start, middle and end of manufacturing of the capsules in Example 5.

The bulk mix samples taken from the hopper (as described above) were not tested, as the content uniformity results for individual capsules were within 90% to 100%. The content uniformity results are detailed in Table 38, Table 39 and FIG. 4 for the start, middle and end of the manufacturing run. The content uniformity results met the acceptance criteria of having an average variation (AV) of less than 15. All individual results are within 90% to 110. Capsules produced in the middle of the run showed very good consistency with an AV of 2.4. Capsules produced at the end of the run showed good consistency also with an AV of 5.5. All the results showed acceptability variability and were all within the AV limit (less than 15). No notable relationship was shown across all samples between capsule fill weight and cobitolimod concentration (Table 39).

TABLE 38

Content uniformity assay results

| Replicate | Content Uniformity (%) | | |
|---|---|---|---|
| | START | MIDDLE | END |
| 1 | 109.6 | 100.0 | 98.7 |
| 2 | 106.4 | 99.6 | 95.8 |
| 3 | 107.0 | 99.7 | 97.8 |
| 4 | 106.8 | 101.2 | 96.4 |
| 5 | 108.2 | 101.2 | 96.3 |
| 6 | 102.7 | 101.6 | 97.1 |
| 7 | 104.8 | 101.0 | 97.4 |
| 8 | 100.5 | 102.8 | 94.8 |
| 9 | 104.3 | 101.8 | 96.0 |
| 10 | 104.3 | 101.4 | 100.9 |
| Mean | 105.4 | 101.0 | 97.1 |
| % RSD | 2.5 | 1 | 1.8 |
| AV | 10.4 | 2.4 | 5.5 |
| AV limit | 15 | 15 | 15 |

TABLE 39

Content uniformity capsules weights

| Replicate | Capsule weights (mg) | | |
|---|---|---|---|
| | START | MIDDLE | END |
| 1 | 443.30 | 452.29 | 450.25 |
| 2 | 446.90 | 452.71 | 445.25 |
| 3 | 451.75 | 449.09 | 446.27 |
| 4 | 451.85 | 451.08 | 443.89 |
| 5 | 449.57 | 454.45 | 444.27 |
| 6 | 433.26 | 449.80 | 445.58 |
| 7 | 446.63 | 450.22 | 445.42 |
| 8 | 444.62 | 455.18 | 448.58 |
| 9 | 448.01 | 448.34 | 445.71 |
| 10 | 440.20 | 453.50 | 447.71 |
| Mean | 445.61 | 451.67 | 446.29 |
| % RSD | 1.3 | 0.5 | 0.4 |

5.9 pH Assessment Results

The bulk mix was sampled as section 5.2 and the results of the pH assessment of the bulk mix at the start, middle and end of the run are detailed in Table 40 below. The pH was maintained at between 7.62 and 7.88 throughout the run which indicated pH consistency with the Tromethamine buffer inclusion. The bulk mix pH was consistent with previous assessments of Tromethamine in Capryol PGMC, as well as an uncoated whole capsule dissolved in deionised water, which gave pH results of between 7.6 and 7.8.

TABLE 40 pH assessment results

| Sample | pH |
|---|---|
| Bulk mix start of filling run | 7.80 |
| Bulk mix middle of filling run | 7.88 |
| Bulk mix end of filling run | 7.62 |

5.10 Conclusion

The capsules were filled, banded and coated successfully, without any significant issues. Due to the low density and physical nature of the API, the API was added to the vessel portionwise. The content uniformity results met the acceptance criteria of AV of less than 15. All individual results are within 90% to 110%.

The assay and related substance data generated, demonstrated that the API was stable during the manufacturing process, as the content of related substances in the final product were comparable to the related substances reported in the starting materials. In addition, the resulting dissolution profile, see FIG. 5, of the capsules from the up-scaled manufacturing was consistent with results obtained in previous Examples.

Example 6—Stability Testing

The capsules packaged in blister packing described in Example 5 above were subjected to testing to assess the stability of the API during long-term storage. Capsules were either stored at 25° C. 60% relative humidity (RH), or at 40° C., 75% relative humidity.

The total impurities and release profiles for the API were recorded at the outset, after one month and after six months. Total impurities were established using HPLC as discussed for Example 3, section 3.4 above. The release profiles were recorded as for the dissolution testing in Example 4, section 4.7 and Example 5 above.

TABLE 41

Impurity assessment results

| Time point | 25° C./60% RH | 40° C./75% RH |
|---|---|---|
| Initial | 3.6 | 3.6 |
| 1 month | 4.0 | 3.6 |
| 6 months | 5.8 | 7.0 |

Table 41 shows the results for total impurities for the timepoints investigated. The low amount of degradation after six months shows that the capsules are suitable for long term storage.

Figure 6:
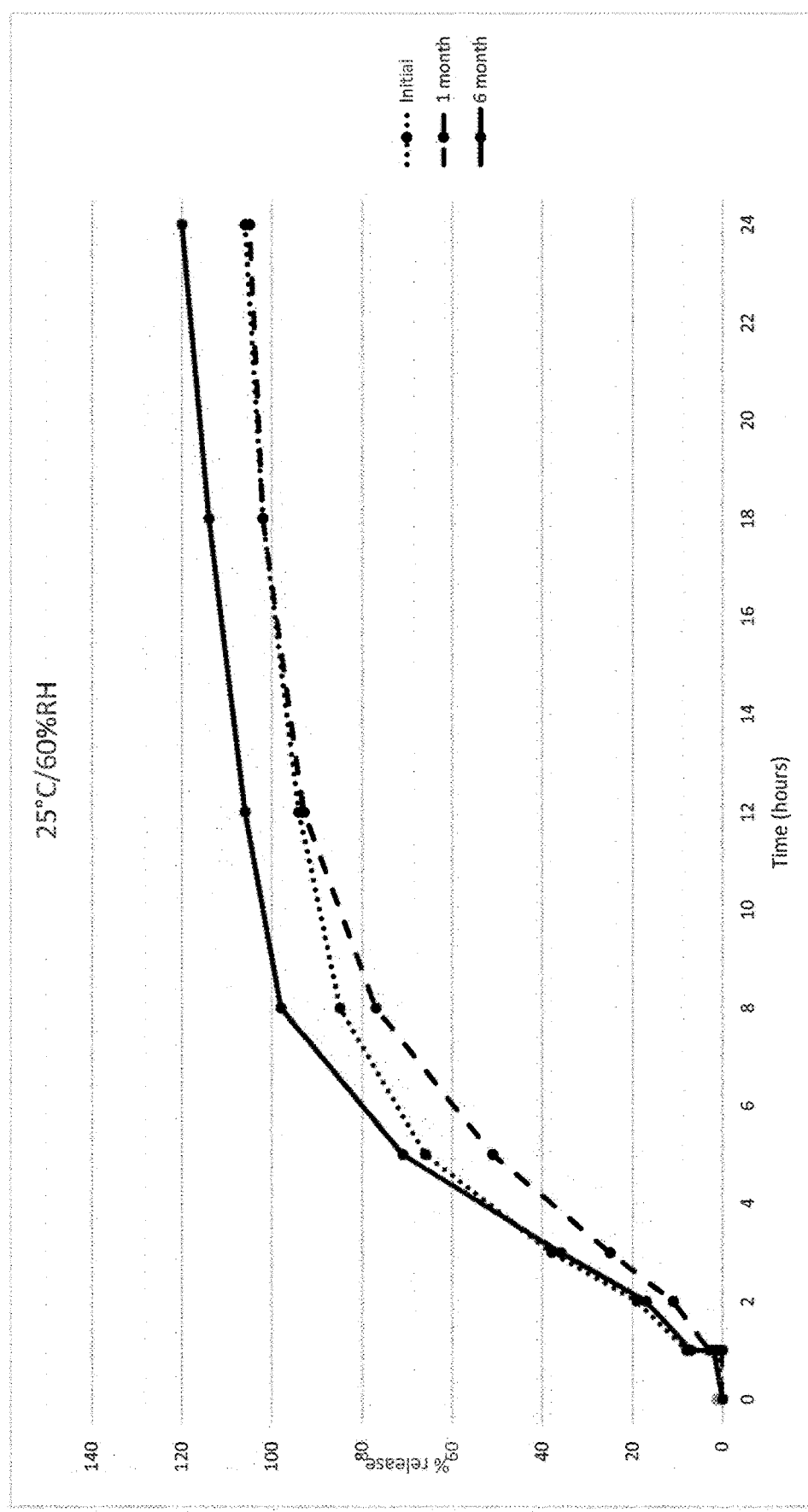
FIG. 6 shows the results of release experiments (dissolution testing) for the capsules of Example 5 at the outset (dotted line), following storage at 25° C./60% relative humidity for one month (dashed line) and following storage at 25° C./60% relative humidity for six months (solid line).

FIG. 6 shows the release profile for the API from the capsules at the beginning of the test (dotted line), after storage for one month at 25° C./60% RH (dashed line) and after storage at six months at 25° C./60% RH (solid line).

Figure 7:
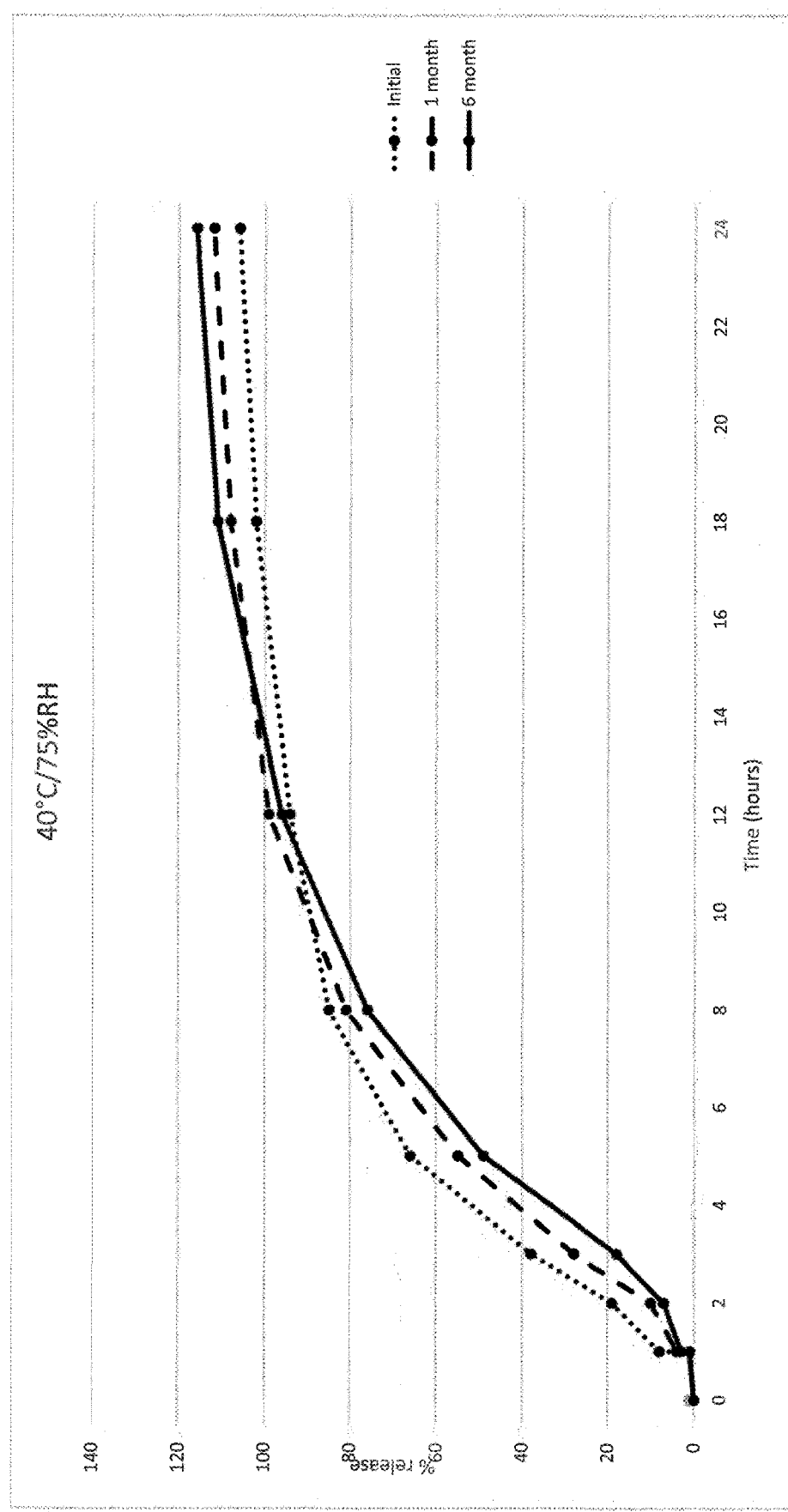
FIG. 7 shows the results of release experiments (dissolution testing) for the capsules of Example 5 at the outset (dotted line), following storage at 40° C./75% relative humidity for one month (dashed line) and following storage at 40° C./75% relative humidity for six months (solid line).

FIG. 7 shows the release profile for the API from the capsules at the beginning of the test (dotted line), after storage for one month at 40° C./75% RH (dashed line) and after storage at six months at 40° C./75% RH (solid line).

Both FIGS. 6 and 7 shown that the release profile for the API does not change over time in the storage periods investigated. This indicates that the contents of the capsules remain stable over time and retain their release characteristics. Moreover, this is even the case when the storage conditions are non-ideal, as is the case for the capsules stored at elevated temperature (40° C.) and relative humidity (75%). In conclusion, the results in Example 6 demonstrate that the capsules have good stability over the long term and retain their release characteristics.

SEQUENCE LISTINGS

SEQ ID NO: 1
5'-G*G*A*ACAGTTCGTCCAT*G*G*C-3', wherein the asterisk (*) indicates a phosphorothioate linkage

SEQ ID NO: 2
5'-GGAACAGTTCGTCCATGGC-3'

The invention claimed is:

1. A formulation suitable for oral administration comprising (i) an oligonucleotide containing a CpG dinucleotide and having 19 to 40 nucleotides, wherein the oligonucleotide comprises the sequence 5'-GGAACAGTTCGTCCATGGC-3' (SEQ ID NO:2), and (ii) esters which are monoesters and/or diesters of propylene glycol with caprylic acid or monoesters and/or diesters of glycerol with caprylic acid.

2. The formulation according to claim 1, wherein at least one CG dinucleotide is unmethylated.

3. The formulation according to claim 1, wherein at least one nucleotide in said oligonucleotide has a backbone modification.

4. The formulation according to claim 1, wherein said oligonucleotide has the sequence 5'-GGAACAGTTCGTCCATGGC-3' (SEQ ID NO:2), wherein the CG dinucleotide is unmethylated.

5. The formulation according to claim 1, wherein (ii) the esters are monoesters and/or diesters of propylene glycol with caprylic acid.

6. The formulation according to claim 1, wherein the formulation further comprises
   i. a gelling agent;
   ii. an antioxidant; and/or
   iii. a pH buffer.

7. A capsule suitable for oral administration, said capsule comprising:
   a) a gelatin container, and within the container b) a formulation comprising (i) an oligonucleotide containing a CpG dinucleotide and having 19 to 40 nucleotides, wherein the oligonucleotide comprises the sequence 5'-GGAACAGTTCGTCCATGGC-3' (SEQ ID NO:2), and (ii) esters which are monoesters and/or diesters of propylene glycol with caprylic acid or monoesters and/or diesters of glycerol with caprylic acid.

8. The capsule according to claim 7, further comprising c) a coating on the exterior surface of the container.

9. The capsule according to claim 8, wherein the coating comprises a first polymer and a second polymer.

10. The capsule according to claim 9, wherein the first polymer is poly(methacrylic acid-co-ethyl acrylate) 1:1 and the second polymer is poly(methyl acrylate-co-methyl methacrylate-co-methacrylic acid) 7:3:1.

11. The capsule according to claim 10, wherein the poly(methacrylic acid-co-ethyl acrylate) 1:1 and poly(methyl acrylate-co-methyl methacrylate-co-methacrylic acid) 7:3:1 are present in a weight ratio of from 5:1 to 1:5, preferably in a weight.

12. The capsule according to claim 9, wherein the first polymer is soluble above pH 5.5 and the second polymer is soluble above pH 7.

13. The capsule according to claim 8, wherein the coating is obtainable by coating the capsule in a coating solution, said coating solution comprising a first polymer and a second polymer, wherein the first polymer is poly(methacrylic acid-co-ethyl acrylate) 1:1 and the second polymer is poly(methyl acrylate-co-methyl methacrylate-co-methacrylic acid) 7:3:1.

14. The capsule according to claim 7, wherein said capsule is configured to release the oligonucleotide at the ileo-cecal junction.

15. The capsule according to claim 7, wherein said capsule is configured to release the oligonucleotide at pH 6.5 to 7.5.

16. The capsule according to claim 7, wherein said capsule is configured to release the oligonucleotide in the ileum.

17. The capsule according to claim 7, wherein said capsule is configured to release the oligonucleotide at pH 5.5 to 6.

18. A method of treating inflammatory bowel disease in a subject, the method comprising orally administering to said subject a) a formulation comprising an oligonucleotide containing (i) a CpG dinucleotide and having 19 to 40 nucleotides, wherein the oligonucleotide comprises the sequence 5'-GGAACAGTTCGTCCATGGC-3' (SEQ ID NO:2); and (ii) esters which are monoesters and/or diesters of propylene glycol with caprylic acid or monoesters and/or diesters of glycerol with caprylic acid; or b) a capsule comprising:
i) a gelatin container, and within the container
ii) a formulation comprising an oligonucleotide containing a CpG dinucleotide and having 19 to 40 nucleotides, wherein the oligonucleotide comprises the sequence 5'-GGAACAGTTCGTCCATGGC-3' (SEQ ID NO:2); and esters which are monoesters and/or diesters of propylene glycol with caprylic acid or monoesters and/or diesters of glycerol with caprylic acid.

19. The formulation according to claim 1, wherein said oligonucleotide has the sequence 5'-G*G*A*ACAGTTCGTCCAT*G*G*C-3' (SEQ ID NO:1) and wherein the CG dinucleotide is unmethylated, wherein * represents a phosphorothioate linkage.

20. The formulation according to claim 1, wherein said oligonucleotide is cobitolimod.

21. The formulation according to claim 1, wherein (ii) the esters comprise between 55 and 80% by weight propylene glycol monocaprylate and between 20 and 45% by weight propylene glycol dicaprylate, relative to the total weight of esters.

22. The formulation according to claim 6, wherein:
i. the gelling agent is hydroxypropyl methyl cellulose (HMPC);
ii. the antioxidant is butylated hydroxytoluene (BHT); and/or
iii. the pH buffer is tromethamine.

23. The formulation according to claim 10, wherein the poly(methacrylic acid-co-ethyl acrylate) 1:1 and poly(methyl acrylate-co-methyl methacrylate-co-methacrylic acid) 7:3:1 are present in a weight ratio of from 1:1 to 1:3.

24. The capsule according to claim 7, wherein said capsule is configured to release the oligonucleotide at pH 6.5 to 6.8 over a period of from 5 to 12 hours.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: SEQ ID NO: 1 Cobitolimod
<220> FEATURE:
<221> NAME/KEY: misc_feature
<222> LOCATION: (1)..(4)
<223> OTHER INFORMATION: phosphorothioate linkage between bases: 1-2,
      2-3 and 3-4
<220> FEATURE:
<221> NAME/KEY: misc_feature
<222> LOCATION: (16)..(20)
<223> OTHER INFORMATION: phosphorothioate linkage between bases: 16-17,
      17-18 and 18-19

<400> SEQUENCE: 1
ggaacagttc gtccatggc                                               19

<210> SEQ ID NO 2
<211> LENGTH: 19
<212> TYPE: DNA
<213> ORGANISM: Artificial Sequence
<220> FEATURE:
<223> OTHER INFORMATION: SEQ ID NO: 2 - synthesized oligonucleotide

<400> SEQUENCE: 2
ggaacagttc gtccatggc                                               19
```